(12) United States Patent
Hadba et al.

(10) Patent No.: US 8,888,810 B2
(45) Date of Patent: *Nov. 18, 2014

(54) COMPOUND BARB MEDICAL DEVICE AND METHOD

(75) Inventors: Ahmad Robert Hadba, Middlefield, CT (US); Gerald Hodgkinson, Guilford, CT (US); Seth Gleiman, Branford, CT (US); Matthew D. Cohen, Berlin, CT (US); Nicholas Maiorino, Branford, CT (US); Timothy D. Kosa, Hamden, CT (US); Mark S. Buchter, Ansonia, CT (US); Michael Primavera, Orange, CT (US)

(73) Assignee: Covidien LP, Mansfield, MA (US)

( * ) Notice: Subject to any disclaimer, the term of this patent is extended or adjusted under 35 U.S.C. 154(b) by 531 days.

This patent is subject to a terminal disclaimer.

(21) Appl. No.: 12/726,815

(22) Filed: Mar. 18, 2010

(65) Prior Publication Data

US 2010/0211097 A1  Aug. 19, 2010

Related U.S. Application Data

(63) Continuation-in-part of application No. 12/361,962, filed on Jan. 29, 2009.

(60) Provisional application No. 61/029,964, filed on Feb. 20, 2008.

(51) Int. Cl.
*A61B 17/08* (2006.01)
*A61B 17/064* (2006.01)
*A61B 17/00* (2006.01)
*A61B 17/06* (2006.01)

(52) U.S. Cl.
CPC . *A61B 17/06166* (2013.01); *A61B 2017/00004* (2013.01); *A61B 2017/00893* (2013.01); *A61B 2017/06176* (2013.01); *A61B 2017/00526* (2013.01); *A61B 17/064* (2013.01)
USPC .......................................................... 606/213

(58) Field of Classification Search
USPC ......... 606/228–231, 75, 86 R, 157, 213, 215, 606/219, 221
See application file for complete search history.

(56) References Cited

U.S. PATENT DOCUMENTS

| 3,123,077 A | 3/1964 | Alcamo |
| 3,657,056 A | 4/1972 | Winston et al. |

(Continued)

FOREIGN PATENT DOCUMENTS

| EP | 0 326 426 A2 | 8/1989 |
| EP | 0 499 048 | 8/1992 |

(Continued)

OTHER PUBLICATIONS

European Search Report for Application No. EP 08 25 3618 dated Jul. 25, 2011.

(Continued)

*Primary Examiner* — Gregory Anderson

(57) ABSTRACT

Barbed medical devices include a crown interconnecting a pair of legs and at least one barb extending from each of the legs. The at least one barb may define an inner surface with a first portion disposed at a first orientation relative to a longitudinal axis of the leg, a second portion disposed at a second orientation relative to the longitudinal axis, and optionally, a third portion disposed at a third orientation relative to the longitudinal axis of the leg.

22 Claims, 13 Drawing Sheets

(56) References Cited

U.S. PATENT DOCUMENTS

| | | |
|---|---|---|
| 3,729,008 A | 4/1973 | Berkovits |
| 3,890,977 A | 6/1975 | Wilson |
| 4,024,871 A | 5/1977 | Stephenson |
| 4,321,002 A | 3/1982 | Froehlich |
| 4,719,917 A | 1/1988 | Barrows et al. |
| 4,738,666 A | 4/1988 | Fuqua |
| 5,019,093 A | 5/1991 | Kaplan et al. |
| 5,059,213 A | 10/1991 | Chesterfield et al. |
| 5,071,429 A | 12/1991 | Pinchuk et al. |
| 5,123,913 A | 6/1992 | Wilk et al. |
| 5,133,738 A | 7/1992 | Korthoff et al. |
| 5,181,923 A | 1/1993 | Chesterfield et al. |
| 5,226,912 A | 7/1993 | Kaplan et al. |
| 5,236,563 A | 8/1993 | Loh |
| 5,258,000 A | 11/1993 | Gianturco |
| 5,261,886 A | 11/1993 | Chesterfield et al. |
| 5,269,783 A * | 12/1993 | Sander ............ 606/148 |
| 5,279,564 A | 1/1994 | Taylor |
| 5,306,289 A | 4/1994 | Kaplan et al. |
| 5,318,575 A | 6/1994 | Chesterfield et al. |
| 5,342,376 A | 8/1994 | Ruff |
| 5,370,031 A | 12/1994 | Koyfman et al. |
| 5,383,387 A | 1/1995 | Chesterfield et al. |
| 5,383,883 A | 1/1995 | Wilk et al. |
| 5,415,635 A | 5/1995 | Bagaoisan et al. |
| 5,417,700 A | 5/1995 | Egan |
| 5,423,858 A | 6/1995 | Bolanos et al. |
| 5,468,248 A | 11/1995 | Chin et al. |
| 5,569,302 A | 10/1996 | Proto et al. |
| 5,620,452 A * | 4/1997 | Yoon ............ 606/151 |
| 5,662,682 A | 9/1997 | Chesterfield et al. |
| 5,667,528 A | 9/1997 | Colligan |
| 5,683,417 A | 11/1997 | Cooper |
| 5,814,056 A | 9/1998 | Prosst et al. |
| 5,893,880 A | 4/1999 | Egan et al. |
| 5,931,855 A | 8/1999 | Buncke |
| 5,964,765 A | 10/1999 | Fenton, Jr. et al. |
| 5,968,069 A | 10/1999 | Dusbabek et al. |
| 6,063,105 A | 5/2000 | Totakura |
| 6,106,505 A | 8/2000 | Modak et al. |
| 6,143,352 A | 11/2000 | Clark et al. |
| 6,159,139 A | 12/2000 | Chiu |
| 6,165,202 A | 12/2000 | Kokish et al. |
| 6,171,299 B1 | 1/2001 | Bonutti |
| 6,174,324 B1 | 1/2001 | Egan et al. |
| 6,203,564 B1 | 3/2001 | Hutton et al. |
| 6,217,591 B1 | 4/2001 | Egan et al. |
| 6,235,869 B1 | 5/2001 | Roby et al. |
| 6,241,747 B1 | 6/2001 | Ruff |
| 6,286,746 B1 | 9/2001 | Egan et al. |
| 6,325,805 B1 * | 12/2001 | Ogilvie et al. ............ 606/75 |
| 6,358,266 B1 | 3/2002 | Bonutti |
| 6,388,043 B1 | 5/2002 | Langer et al. |
| 6,488,690 B1 | 12/2002 | Morris et al. |
| 6,506,197 B1 | 1/2003 | Rollero et al. |
| 6,524,283 B1 | 2/2003 | Hopper et al. |
| 6,551,282 B1 | 4/2003 | Exline et al. |
| 6,562,051 B1 | 5/2003 | Bolduc et al. |
| 6,589,208 B2 | 7/2003 | Ewers et al. |
| 6,599,310 B2 | 7/2003 | Leung et al. |
| 6,620,846 B1 | 9/2003 | Jonn et al. |
| 6,626,916 B1 | 9/2003 | Yeung |
| 6,692,499 B2 | 2/2004 | Tormala et al. |
| 6,773,450 B2 | 8/2004 | Leung et al. |
| 6,923,824 B2 | 8/2005 | Morgan et al. |
| 7,090,111 B2 | 8/2006 | Egan et al. |
| 7,341,571 B1 | 3/2008 | Harris et al. |
| 2002/0077661 A1 | 6/2002 | Saadat |
| 2002/0095169 A1 | 7/2002 | Maitland et al. |
| 2002/0177876 A1 | 11/2002 | Roby et al. |
| 2003/0074023 A1 | 4/2003 | Kaplan et al. |
| 2003/0097148 A1 | 5/2003 | Valimaa et al. |
| 2003/0149447 A1 | 8/2003 | Morency et al. |
| 2003/0236445 A1 | 12/2003 | Couvillon |
| 2003/0236531 A1 | 12/2003 | Couvillon |
| 2003/0236533 A1 | 12/2003 | Wilson et al. |
| 2003/0236534 A1 | 12/2003 | Kayan |
| 2004/0010275 A1 | 1/2004 | Jacobs et al. |
| 2004/0030354 A1 | 2/2004 | Leung et al. |
| 2004/0060409 A1 | 4/2004 | Leung et al. |
| 2004/0060410 A1 | 4/2004 | Leung et al. |
| 2004/0087974 A1 | 5/2004 | Bittar |
| 2004/0088003 A1 | 5/2004 | Leung et al. |
| 2004/0122451 A1 | 6/2004 | Wood |
| 2004/0138702 A1 | 7/2004 | Peartree et al. |
| 2004/0138705 A1 * | 7/2004 | Heino et al. ............ 606/219 |
| 2004/0153125 A1 | 8/2004 | Roby |
| 2004/0162580 A1 | 8/2004 | Hain |
| 2004/0204723 A1 | 10/2004 | Kayan |
| 2005/0033367 A1 | 2/2005 | Leung et al. |
| 2005/0049635 A1 | 3/2005 | Leiboff |
| 2005/0082826 A1 | 4/2005 | Werth |
| 2005/0149062 A1 | 7/2005 | Carroll |
| 2005/0165448 A1 | 7/2005 | Egan et al. |
| 2005/0171562 A1 | 8/2005 | Criscuolo et al. |
| 2005/0209639 A1 | 9/2005 | Gidwani et al. |
| 2005/0216058 A1 | 9/2005 | Egan et al. |
| 2005/0267479 A1 | 12/2005 | Morgan et al. |
| 2005/0267531 A1 | 12/2005 | Ruff et al. |
| 2005/0273138 A1 | 12/2005 | To et al. |
| 2006/0111734 A1 | 5/2006 | Kaplan et al. |
| 2006/0116718 A1 | 6/2006 | Leiboff |
| 2006/0135995 A1 | 6/2006 | Ruff et al. |
| 2006/0206096 A1 | 9/2006 | Accisano, III et al. |
| 2007/0005110 A1 | 1/2007 | Collier et al. |
| 2007/0021780 A1 | 1/2007 | Harrington et al. |
| 2007/0038238 A1 | 2/2007 | Freeman et al. |
| 2007/0106319 A1 | 5/2007 | Au et al. |
| 2007/0133103 A1 | 8/2007 | Genova et al. |
| 2007/0187861 A1 | 8/2007 | Genova |
| 2007/0203517 A1 | 8/2007 | Williams et al. |
| 2007/0208276 A1 | 9/2007 | Kornkven Volk et al. |
| 2007/0225651 A1 | 9/2007 | Rosenberg et al. |
| 2008/0015598 A1 | 1/2008 | Prommersberger |
| 2008/0312688 A1 * | 12/2008 | Nawrocki et al. ............ 606/228 |
| 2009/0105655 A1 | 4/2009 | DeSantis et al. |
| 2009/0105659 A1 | 4/2009 | Bettuchi et al. |
| 2009/0105691 A1 | 4/2009 | Sung |

FOREIGN PATENT DOCUMENTS

| | | |
|---|---|---|
| EP | 0 632 999 A | 1/1995 |
| EP | 0 647 452 | 4/1995 |
| EP | 1 669 093 | 6/2006 |
| EP | 1747759 | 1/2007 |
| EP | 1747772 | 1/2007 |
| EP | 1878391 | 1/2008 |
| EP | 1 656 890 | 12/2008 |
| EP | 2050404 | 4/2009 |
| EP | 2050405 | 4/2009 |
| EP | 2050406 | 4/2009 |
| EP | 2 106 752 A1 | 10/2009 |
| EP | 2108319 A1 | 10/2009 |
| EP | 2133028 A2 | 12/2009 |
| WO | WO 91/07916 A1 | 6/1991 |
| WO | WO 97/08238 | 3/1997 |
| WO | WO 98/00065 | 1/1998 |
| WO | WO 98/52473 | 11/1998 |
| WO | WO 99/52451 A | 10/1999 |
| WO | WO 00/57933 A1 | 10/2000 |
| WO | WO 01/52751 A | 7/2001 |
| WO | WO 02/00286 | 1/2002 |
| WO | WO 03/001979 A2 | 1/2003 |
| WO | WO 03/088818 A2 | 10/2003 |
| WO | WO 03/088846 A1 | 10/2003 |
| WO | WO 2004/014236 A1 | 2/2004 |
| WO | WO 2004/030520 A2 | 4/2004 |
| WO | WO 2004/030704 A2 | 4/2004 |
| WO | WO 2004/030705 A2 | 4/2004 |
| WO | WO 2004/045663 | 6/2004 |
| WO | WO 2004/052594 | 6/2004 |
| WO | WO 2004/060463 | 7/2004 |
| WO | WO 2004/066927 | 8/2004 |
| WO | WO 2004/105621 | 12/2004 |

(56) References Cited

FOREIGN PATENT DOCUMENTS

| WO | WO 2005/000001 | 1/2005 |
|----|----|----|
| WO | WO 2005/080495 | 1/2005 |
| WO | WO 2006/079469 | 8/2006 |
| WO | WO 2007/038715 | 4/2007 |
| WO | WO 2007/133103 A | 11/2007 |
| WO | 2008/045376 A2 | 4/2008 |
| WO | WO 2008/042909 A | 4/2008 |
| WO | WO 2008/107919 A | 9/2008 |
| WO | WO 2008/141034 A1 | 11/2008 |

OTHER PUBLICATIONS

U.S. Appl. No. 60/994,173, filed Sep. 17, 2007, Maiorino et al.
European Search Report for EP 09250460.4-2310 date of completion is Jun. 2, 2009 (3 pages).
JLT1204-211-229 (175) : R. R. Szarmach et al., Journal of Long-Term Effects of Medical Implants, "An Innovative Surgical Suture and Needle Evaluation and Selection Program" 12(4), pp. 211-229 (2002).
George Odian, "Principles of Polymerization", III Edition, pp. 569-573 (1991).
International Search Report from Appln. No. EP 06 012688 dated Aug. 1, 2007.
European Search Report from Appln. No. EP 07 253438 dated Feb. 1, 2008.
European Search Report from application No. 07 25 4703 dated Feb. 10, 2009.
European Search Report from application No. 07 25 4341 dated Apr. 20, 2009.
European Search Report for EP 09251035.3 dated Jun. 3, 2009.
European Search Report for EP 10177651.6-1526 date of completion is Dec. 14, 2010 (3 pages).
Lendlein, et al., "Shape-memory polymers as stimuli-sensitive implant materials", *Clinical Hemorheology and Microcirculation* 2005, 32:105-116.
Lendlein, et al., "Biodegradable, Elastic Shape-Memory Polymers for Potential Biomedical Applications", *Science* 2002, 296:1673-1676.
Lendlein, "Solving a knotty problem—surgical sutures from shape memorypolymers", *Materials World* 2002, 10(7):29-30.
Small, et al., "Laser-activated shape memory polymer intravascular thrombectomy device", *Optics Express* 2005, 13(20):8204-8213.
Faré, et al., "In vitro interaction of human fibroblasts and platelets with a shape-memory polyurethane", *Fibroblast/Platelet Interaction With SMPu* Wiley Periodicals, Inc. (2005), pp. 1-11.
Tim Thompson, "Polyurethanes as Specialty Chemicals Principles and Applications", 2005 CRC Press, Chapter 2: Polyurethane Chemistry in Brief.
European Search Report for European Application No. 10250002.2 dated Mar. 24, 2010. (9 pages).
European Search Report for EP 12151535.7-2310 date of completion is Mar. 27, 2012 (6 pages).
European Search Report for EP 12151526.6-2310 date of completion is Mar. 23, 2012 (6 pages).
European Search Report for EP 12151532.4-2310 date of completion is Mar. 27, 2012 (6 pages).
European Search Report for EP 12151531.6-2310 date of completion is Mar. 27, 2012 (6 pages).
European Search Report for EP 12151525.8-2310 date of completion is Mar. 27, 2012 (5 pages).
European Search Report for EP 12151530.8-2310 date of completion is Mar. 16, 2012 (6 pages).
European Search Report for EP 12151537.3-2310 date of completion is Mar. 19, 2012 (6 pages).
European Search Report for EP 11250537.1269 date of completion Aug. 8, 2011 (3 pages).

* cited by examiner

COMPOUND BARB MEDICAL DEVICE AND METHOD

CROSS-REFERENCE TO RELATED APPLICATIONS

This application is a continuation-in-part of U.S. patent application Ser. No. 12/361,962, filed Jan. 29, 2009, which claims the benefit of and priority to U.S. Provisional Application No. 61/029,964, filed Feb. 20, 2008, the entire disclosures of each of which are incorporated by reference herein.

TECHNICAL FIELD

The present disclosure relates generally to forming barbs on medical devices. In particular, the present disclosure relates to compound barb medical devices including shape memory polymeric materials, and methods of forming and using such medical devices.

BACKGROUND OF RELATED ART

Barbed sutures are known for use in medical procedures. The configuration of barbs on a barbed suture may be designed to optimize tissue holding for a particular indication. In some circumstances, a random configuration of barbs on the exterior surface of the suture may be preferred to achieve optimal wound closure. However, in other circumstances, where the wound or tissue repair needed is relatively small, a reduced number of barbs may be desired. In still other circumstances, a bidirectional barbed suture may be desirable to permit passing of the suture through tissue in one direction over a portion of the suture and permit passing of the suture through tissue in a second direction over another portion of the suture.

While various methods of forming barbs on sutures have been proposed, such methods may be difficult or costly to implement. Thus, there remains room for improvement with respect to barbed sutures and methods for making them.

Moreover, surgical fasteners or staples may also be used in surgical procedures to fasten body tissue. Typically, a staple is a U-shaped member including a back span and two legs which are bent by a delivery device to hook body tissue together. An anvil of a stapler generally crimps the staple, and thus, conventional staplers typically comprise complex structures which must not only eject the staples but to do so in a manner such that the staple deforms properly and timely.

Two part fasteners have also been used in which a staple includes barbed prongs which engage a separate retainer piece. In use, the staple is pressed into the body tissue so that the barbs penetrate the tissue and emerge from the other side where they are then locked into the retainer piece.

Thus, there remains room for improvement with respect to barbed staples and methods for making them.

SUMMARY

The present disclosure is directed to a compound barb medical device including a crown interconnecting a pair of legs; and at least one barb extending from each of the legs, the at least one barb defining an inner surface, the inner surface including a first portion disposed at a first orientation relative to a longitudinal axis of the leg and a second portion disposed at a second orientation relative to the longitudinal axis. The inner surface of the compound barb medical device may include comprise a third portion disposed at a third orientation relative to the longitudinal axis.

More specifically, the first angle of the compound barb medical device have include the first angle is about 0 degrees to about 90 degrees, in embodiments, from about 30 degrees to about 40 degrees, and in further embodiments, from about 31 degrees to about 38 degrees.

The second angle of the compound barb medical device may be of from about 0 degrees to about 90 degrees, in embodiments, from about 1 degree to about 10 degrees, and in further embodiments, from about 2 degrees to about 8 degrees.

The third angle of the compound barb medical device may be from about 0 degrees to about 90 degrees.

In certain embodiments, at least one of the first, second, and third portions is substantially linear. The compound barb medical device may include at least one of the first, second, and third portions are disposed at first, second, and third angles relative to respective longitudinal axes of each leg. Alternatively, at least one of the first, second, and third portions is substantially non-linear. The non-linear portion may be cut at a radius relative to the longitudinal axis of the leg.

The compound barb medical device may be formed from an absorbable or non-absorbable material. The non absorbable material may be selected from titanium, stainless steel, polyolefins, polyamides, polyamines, polyimines, polyesters, fluoropolymers, polyether-esters, polytetramethylene ether glycol, 1,4-butanediol, polyurethanes, copolymers, and combinations thereof. The absorbable material may comprise a dissolvable metal, polyesters, polyorthoesters, polymer drugs, polydroxybutyrates, dioxanones, lactones, proteins, cat gut, collagens, carbonates, alkylene carbonates, caprolactone, glycolic acid, lactic acid, glycolide, lactide, homopolymers, copolymers, and combinations thereof. Further, the compound barb medical device may comprise a bioactive agent.

A method of forming a compound barb on a staple is also disclosed, including providing a staple having a pair of legs, each leg defining a longitudinal axis; and applying vibrational energy to a cutting element to form a compound barb on at least a portion of each leg including: forming a first cut in the leg, the first cut having a first ratio of cut depth to diameter of the leg; and forming a second cut in the leg, the second cut having a second ratio of cut depth to diameter of the leg.

BRIEF DESCRIPTION OF THE DRAWINGS

Various embodiments of the present disclosure will be described herein below with reference to the figures wherein.

DETAILED DESCRIPTION

Figure 1:
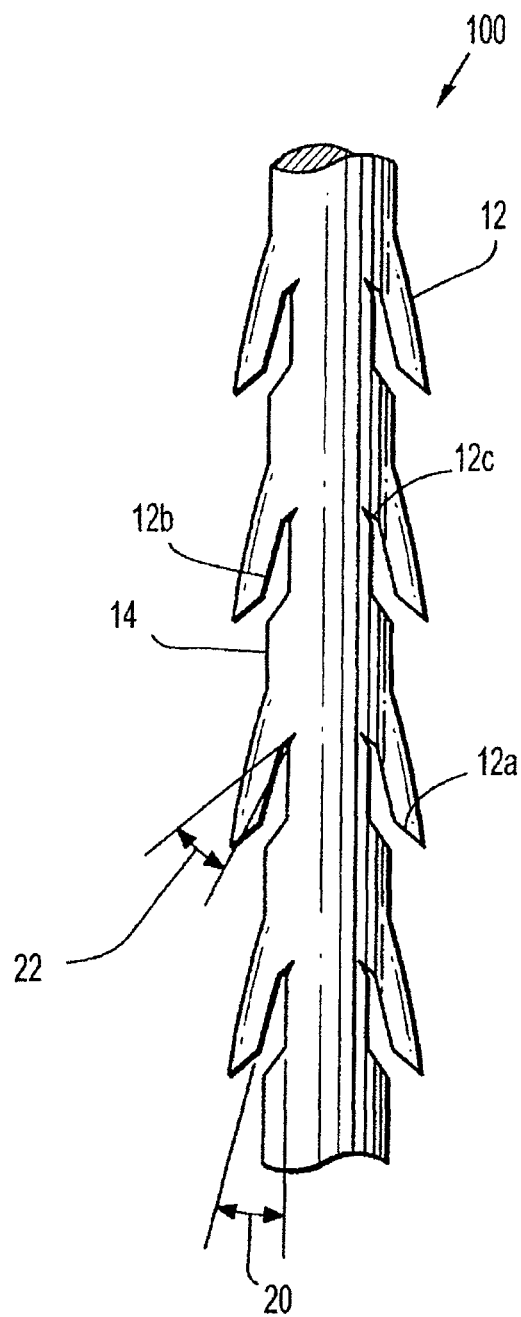
FIG. 1 is a plan view of a barbed medical device having compound barbs formed in accordance with the present disclosure.

Referring in detail to the drawings in which like reference numerals are applied to like elements in the various views, FIG. 1 illustrates a medical device 100 having an elongated body 14 and at least one compound barb 12 extending from the elongated body 14. Compound barb 12 defines an inner surface which includes a first portion 12a disposed at a first orientation relative to the longitudinal axis of elongated body 14, a second portion 12b disposed at a second orientation relative to the longitudinal axis, and a third portion 12c disposed at a third orientation relative to the longitudinal axis.

Compound barbs 12 include at least one substantially linear portion. As illustrated in FIG. 1, first, second and third portions 12a-c are substantially linear. It is envisioned that at least one of the portions may be substantially non-linear, such as for example, arcuate as described hereinbelow.

Figure 2:
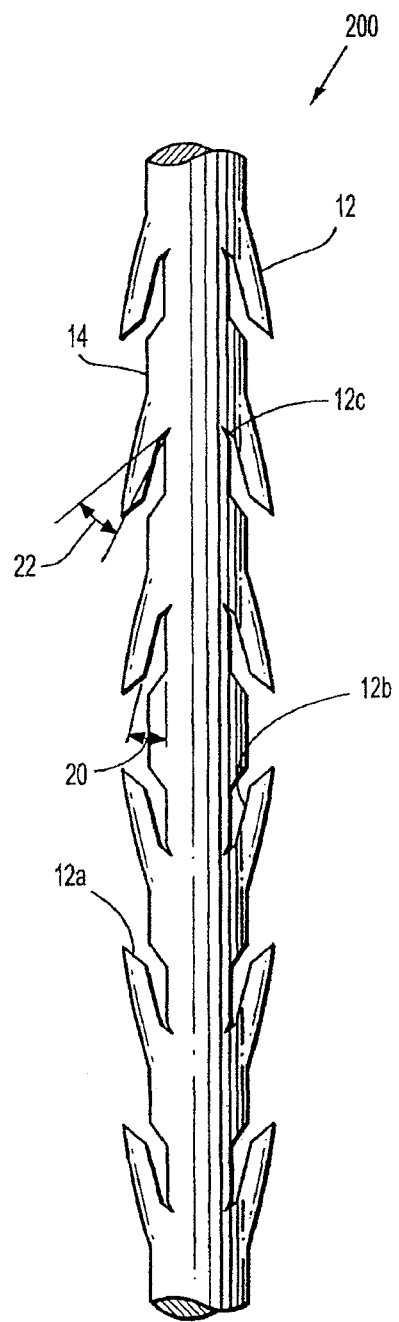
FIG. 2 is a plan view of a two way barbed medical device having compound barbs formed in accordance with the present disclosure.

As shown in the exemplary embodiment of FIG. 1, compound barbs 12 may be formed projecting from the medical device 100 towards at least one end of medical device 100. In other alternative embodiments, multiple compound barbs may be formed such that some of the barbs project toward one end of the medical device and the remaining barbs project toward the other end of the medical device so as to form a bidirectional medical device 200 as generally illustrated in FIG. 2. Alternatively, a plurality of axially spaced barbs may be formed in the same or random configuration and at different angles in relation to each other. Optionally, the medical device may include a plurality of barbs spaced at the same or different lengths according to the type of tissue being manipulated and/or procedure performed (not shown). In some embodiments, the compound barb medical device incorporates a loop at the proximal end thereof configured to enhance retention of the medical device in body tissue at a desired position.

Figure 3:
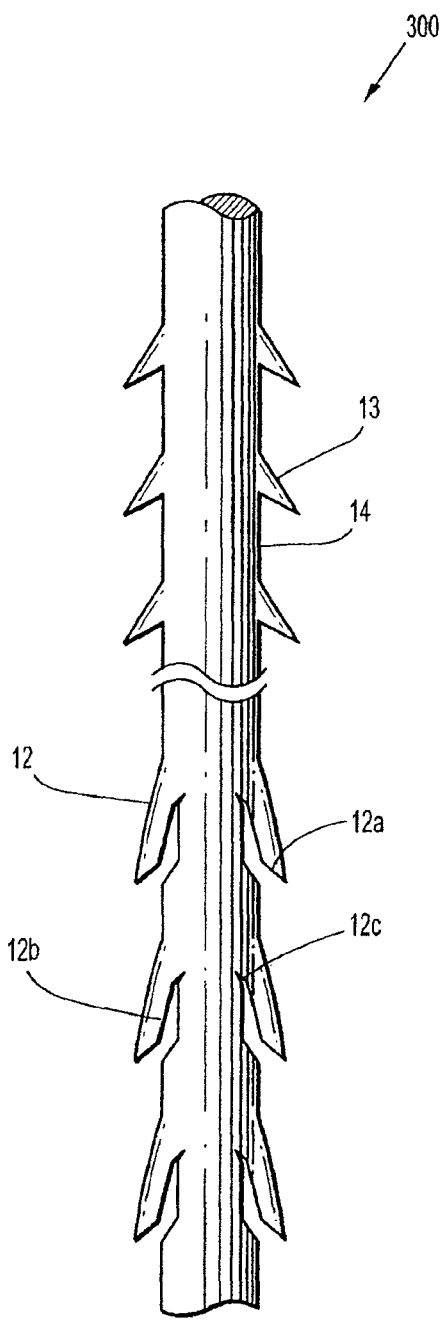
FIG. 3 is a plan view of an alternative embodiment of a barbed medical device having both single angle barbs and compound barbs formed in accordance with the present disclosure.

In an alternative embodiment, medical device 300 may be formed to include a combination of compound barbs 12 and single angle barbs 13 as shown in FIG. 3. In such an embodiment, the compound barbs 12 and single angle barbs 13 may be formed along the length of the medical device 300 in specified or random patterns. Additionally, the medical device 300 may be formed such that compound barbs 12 are all oriented in the same direction toward one end of medical device 300 and the single angle barbs 13 are all oriented in the same direction toward the other end of medical device 300.

Figure 4A:
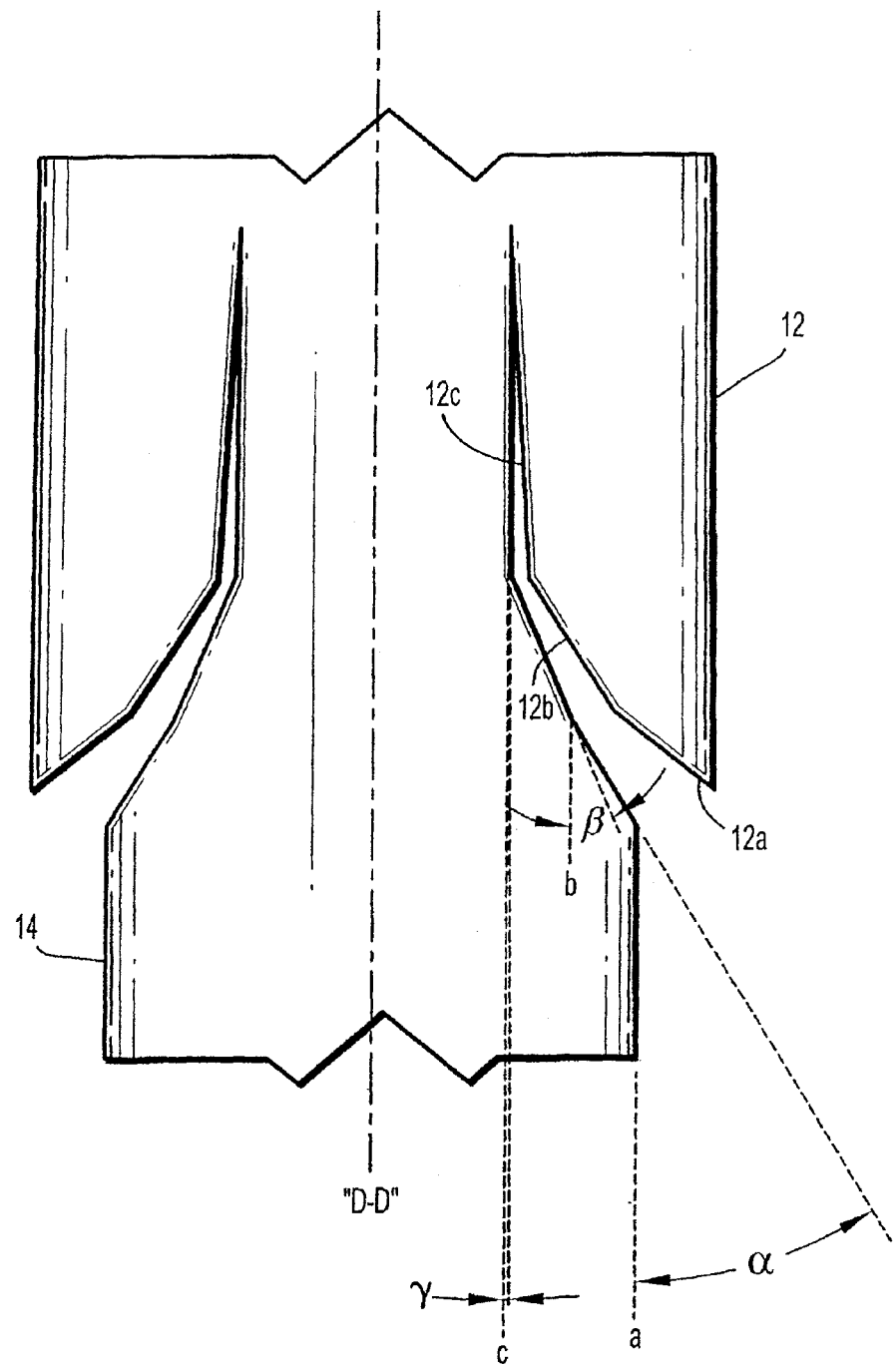
FIG. 4A is a plan view of a segment of a barbed medical having compound barbs formed in accordance with the present disclosure.

Referring to FIG. 4A, compound barbs 12 having first, second and third portions 12a-c are generally formed by cutting into the surface of elongated body 14. In embodiments, each of the first, second, and third portions 12a-c may be cut at first, second and third angles $\alpha$, $\beta$, and $\gamma$ relative to longitudinal axes a, b, and c respectively of elongated body 14. Longitudinal axes a, b, and c are parallel to a central longitudinal axis D', and the second angle $\beta$ is less than the first angle $\alpha$, and the third angle $\gamma$ is less than the second angle $\beta$. Compound barb 12 may include a first portion 12a which is formed by cutting into elongated body 14 at a first angle $\alpha$ of from about 0 degrees to about 90 degrees relative to longitudinal axis "a", in embodiments, the first angle $\alpha$ ranges from about 30 degrees to about 50 degrees relative to longitudinal axis "a". A second portion 12b may be formed by cutting into elongated body 14 at a second angle $\beta$ of from about 0 degrees to about 90 degrees relative to the longitudinal axis "b", in embodiments, the second angle $\beta$ ranges from about 2 degrees to about 25 degrees relative to the longitudinal axis "b". A third portion 12c may be formed by cutting into elongated body 14 at a third angle $\gamma$ of from about 0 degrees to about 90 degrees relative to longitudinal axis "c", in embodiments, the third angle $\gamma$ ranges from about 2 degrees to about 50 degrees relative to longitudinal axis "c".

Figure 4B:
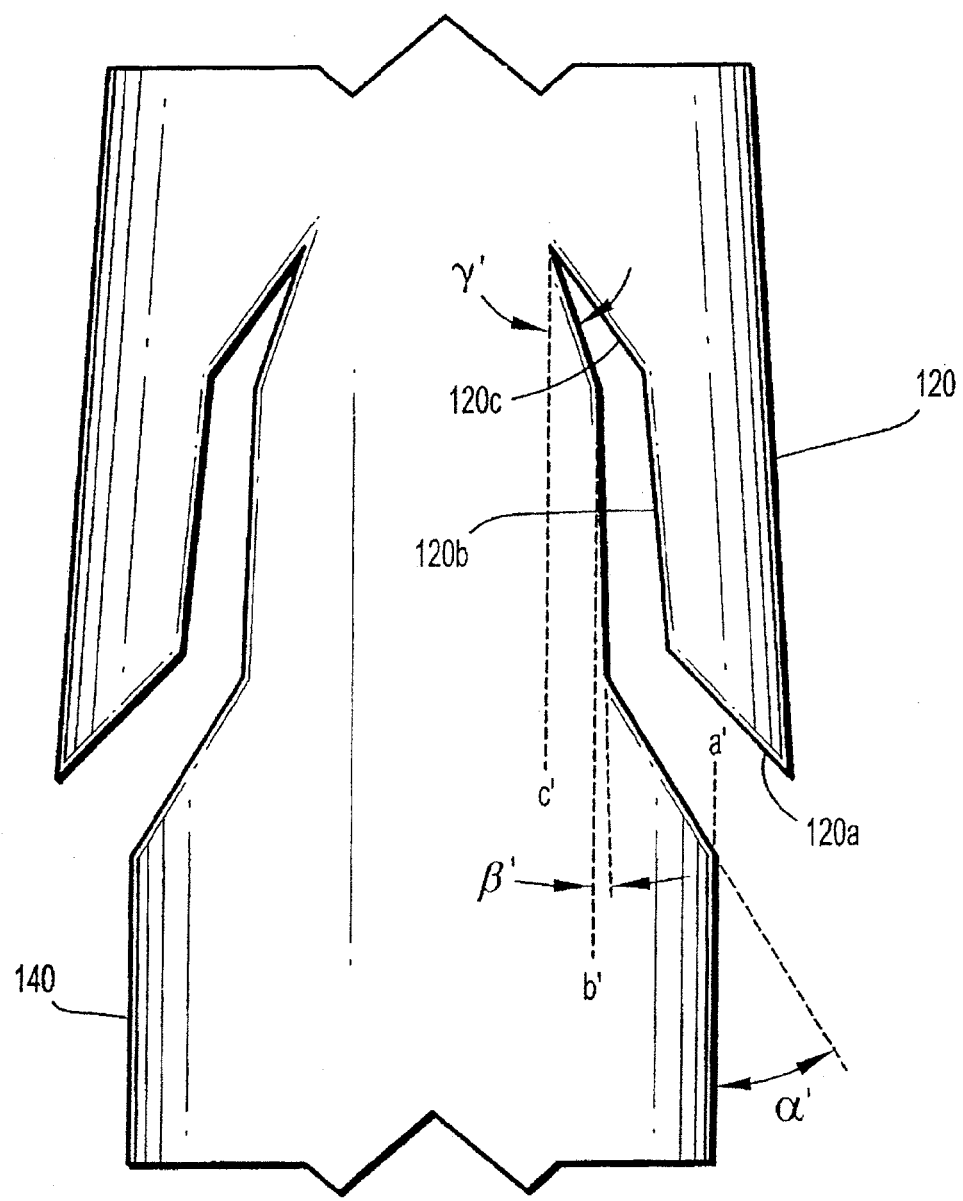
FIG. 4B is a plan view of an alternative embodiment of a segment of a barbed medical having compound barbs formed in accordance with the present disclosure.

Referring now to FIG. 4B, each of the first, second and third portions 12a'-c' may be cut at first, second and third angles $\alpha'$, $\beta'$, and $\gamma'$ relative to the longitudinal axes "a", "b'", and "c", respectively, of elongated body 140, such that angle $\alpha'$ is greater than angle $\beta'$ and angle $\gamma'$ is less than angle $\beta'$. Compound barb 120 may include a first portion 120a which is formed by cutting into elongated body 140 at a first angle $\alpha'$ of from about 0 degrees to about 90 degrees relative to longitudinal axis "a", in embodiments, the first angle $\alpha'$ ranges from about 30 degrees to about 50 degrees relative to longitudinal axis "a". A second portion 120b may be formed by cutting into elongated body 140 at a second angle $\beta'$ of from about 0 degrees to about 90 degrees relative to longitudinal axis "b", in embodiments, the second angle $\beta'$ ranges from about 30 degrees to about 60 degrees relative to longitudinal axis "b". A third portion 12c may be formed by cutting into elongated body 140 at a third angle $\gamma'$ of from about 0 degrees to about 90 degrees relative to longitudinal axis "c", in embodiments, the third angle $\gamma'$ ranges from about 25 degrees to about 50 degrees relative to longitudinal axis "c'".

In other embodiments, a compound barb medical device includes an elongated body having first and second portions, the first and second portions of the elongated body are at first and second angles respective to a longitudinal axis of the elongated body to form at least one compound barb (not shown). Optionally, the elongated body of the compound barb medical device may include a third portion at a third angle respective to a longitudinal axis of the elongated body.

Figure 10:
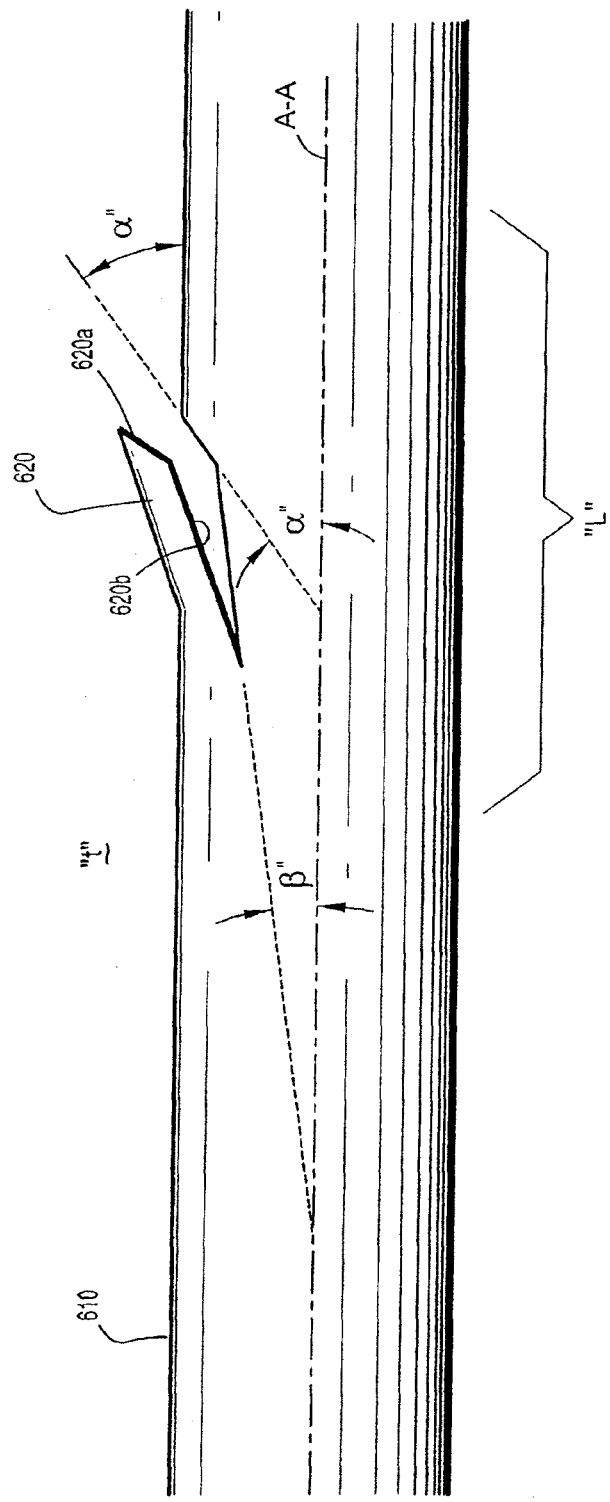
FIG. 10 is a plan view of an alternate embodiment of a segment of a barbed medical device having compound barbs formed in accordance with the present disclosure.

Such an embodiment of a compound barb suture is shown in FIG. 10. The compound barb 620 includes two portions 620a, 620b which are disposed at two angles, $\alpha''$ and $\beta''$ relative to a longitudinal axis of the medical device. More specifically, the compound barb 620 includes a first portion 620a formed from the elongated body 610 at a first angle $\alpha''$, which is from about 0 degrees to about 90 degrees, in embodiments, from about 30 degrees to about 40 degrees, and in further embodiments, from about 31 degrees to about 38 degrees, relative to a longitudinal axis A-A of the elongated body 610. The second portion 620b is formed from the elongated body 610 at a second angle $\beta''$ which is from about 0 degrees to about 90 degrees, in embodiments, from about 1 degrees to about 10 degrees and in further embodiments, from about 2 degree to about 8 degrees relative to the longitudinal axis A-A of the elongated body 610.

Figure 11:
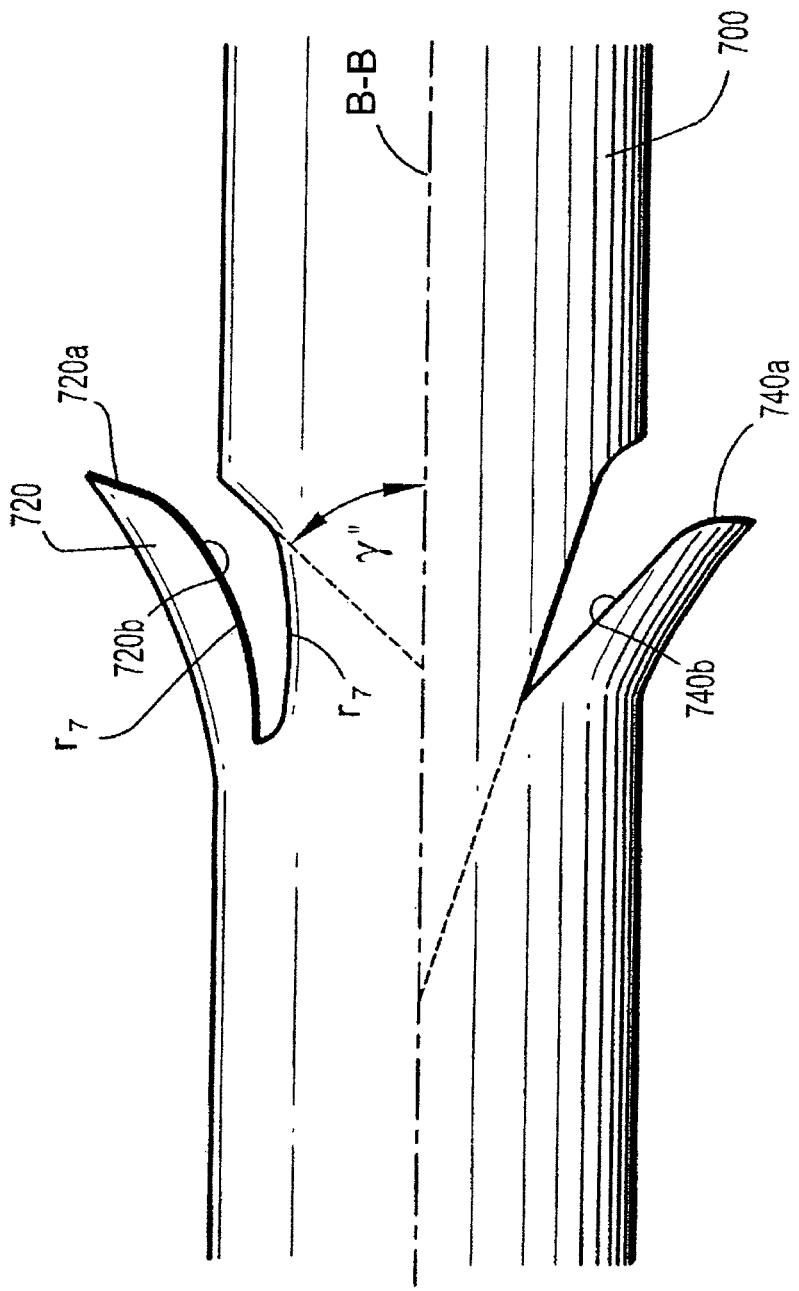
FIG. 11 is a plan view of another embodiment of a segment of a barbed medical device having compound barbs formed in accordance with the present disclosure.

Another embodiment of a compound barb device is shown in FIG. 11. An elongated body 700 is shown including a compound barb 720 having a first linear portion 720a, shown at an angle γ", relative to a longitudinal axis B-B of the elongated body 700. Extending from the first portion 720a is an arcuate second portion 720b at a radius $r_7$. The elongated body 700 also includes a compound barb wherein a first portion 740a is arcuate and a second portion 740b is linear.

Figure 5:
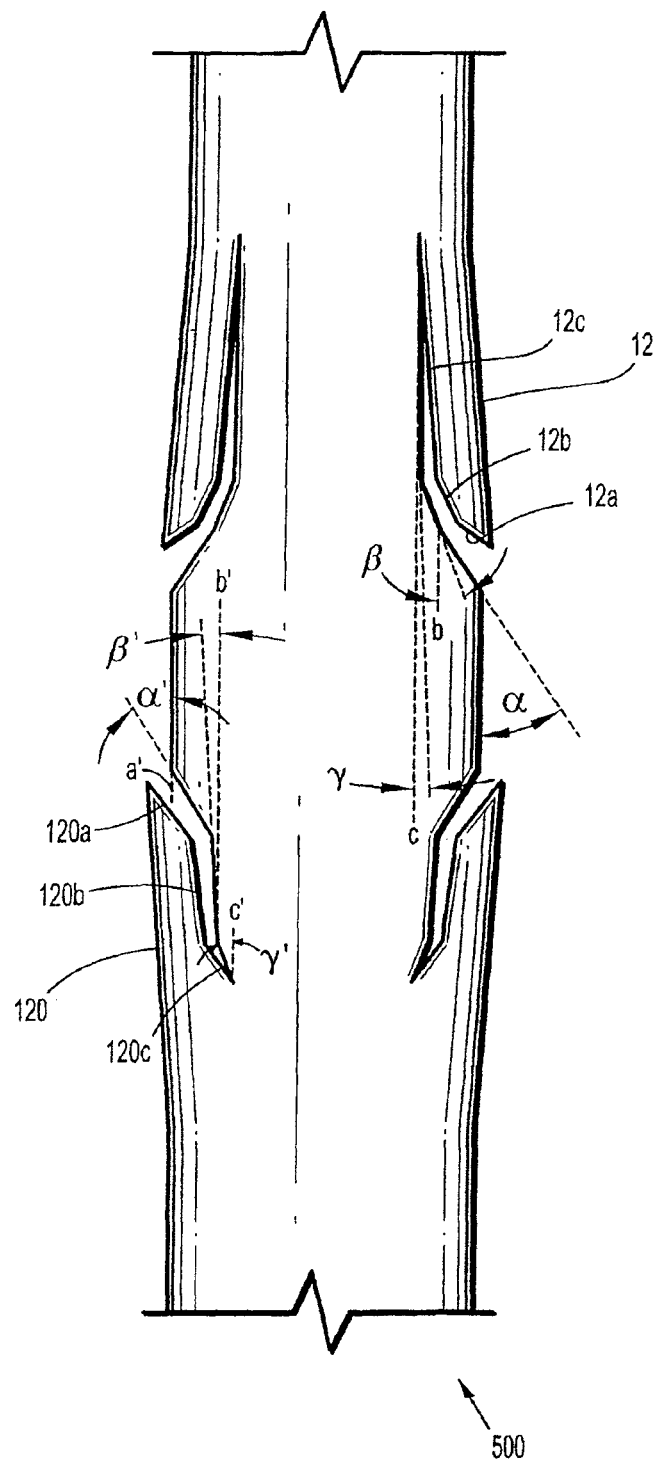
FIG. 5 is a plan view of a segment of a bi-directional barbed medical device having compound barbs formed in accordance with the present disclosure.

FIG. 5 illustrates compound barb 12 having three portions 12a-c, as illustrated in FIG. 4A, and compound barb 120 having three portions 120a'-c' as illustrated in FIG. 4B, formed such that some of the barbs project toward one end of medical device 500 and the remaining barbs project toward the other end of medical device 500 so as to form a bi-directional medical device 500. In alternative embodiments, compound barbs are formed such that the barbs projecting toward one end, for example, towards the proximal end, have the same orientation and angles as the barbs projecting towards the other end, for example, towards the distal end.

Figure 6:
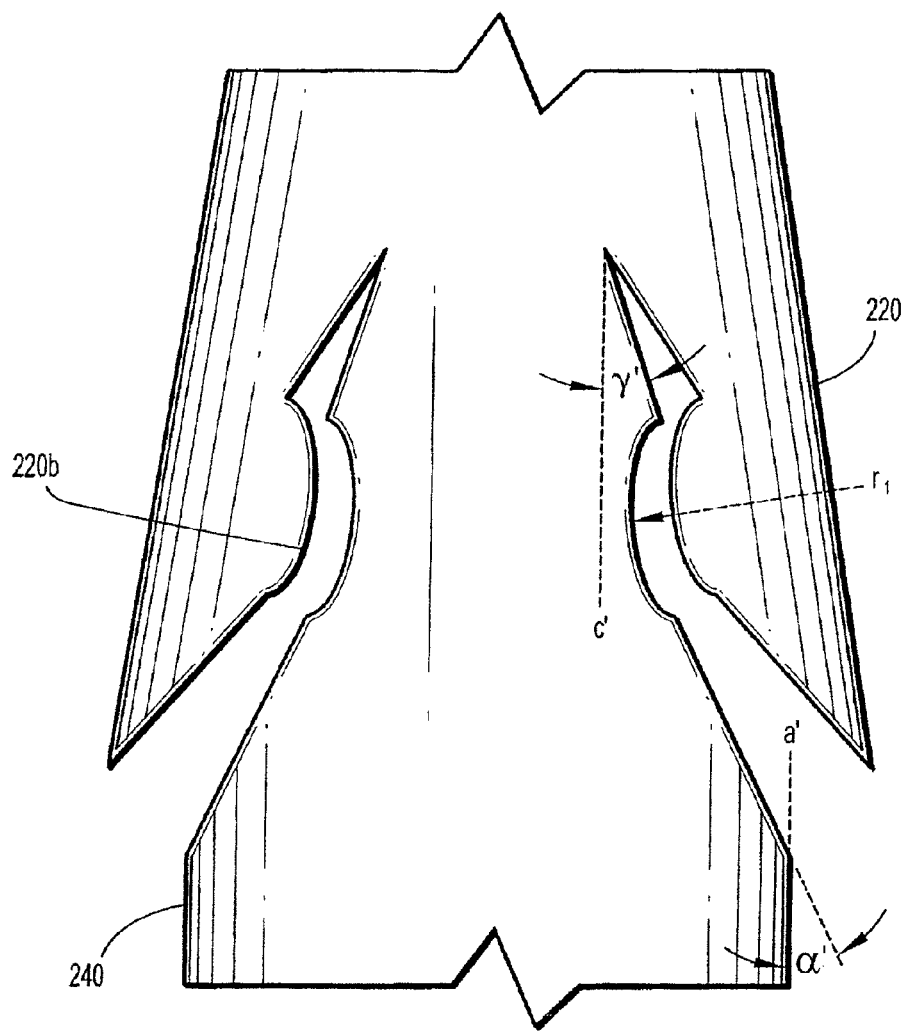
FIG. 6 is a plan view of an alternative embodiment of a barbed medical device having compound barbs formed in accordance with the present disclosure.

In some embodiments, the compound barb may include at least one portion which is substantially non-linear. In embodiments, the barbs may include at least one point of inflection which may define a concave portion, a convex portion, an arcuate portion and combinations thereof. For example, at least one of the portions may be cut at a radius relative to the longitudinal axis of elongated body 240. As shown in FIG. 6, compound barb 220 may include an arcuate second portion 220b. The arcuate portion 220b may be cut at a radius $r_1$ relative to the longitudinal axis of elongated body 240.

Figure 7:
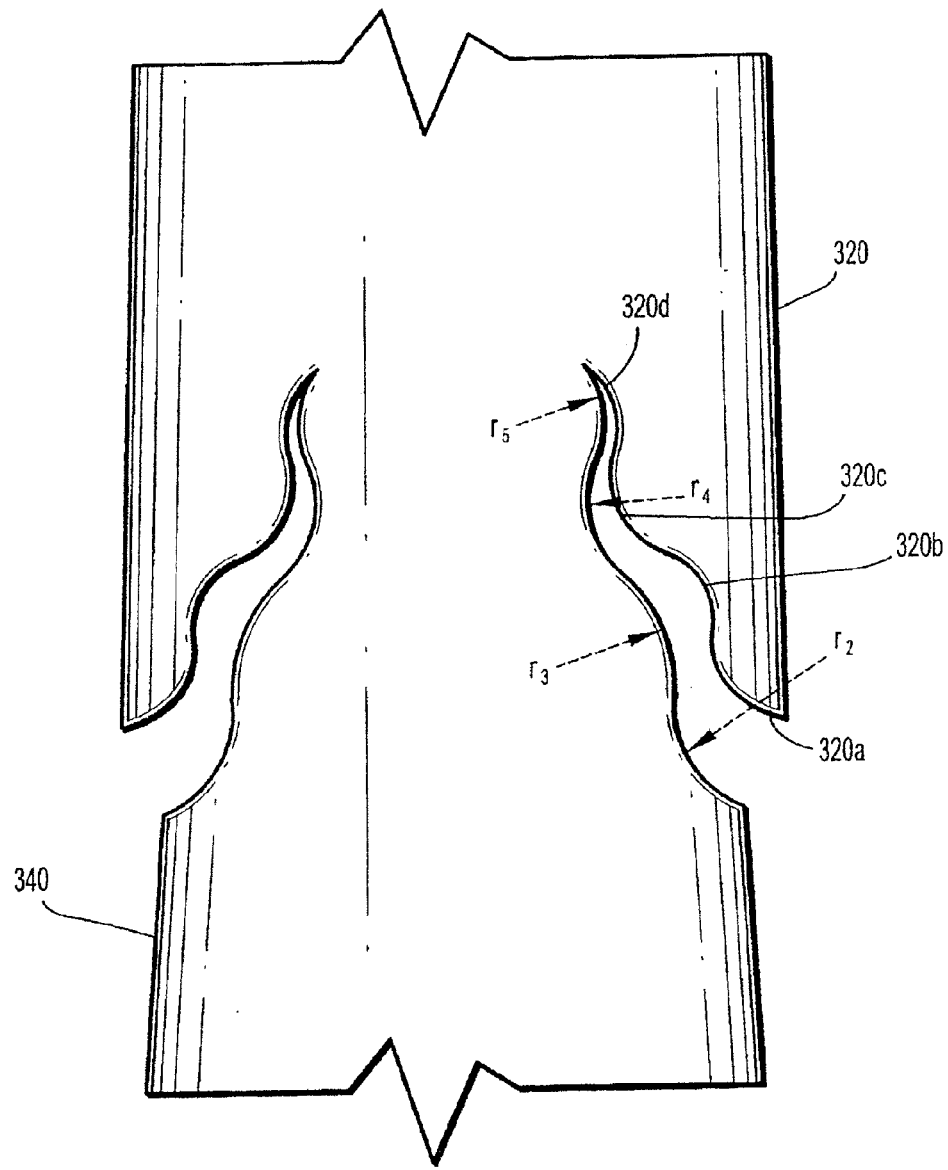
FIG. 7 is a plan view of an alternative embodiment of a barbed medical device having compound barbs formed in accordance with the present disclosure.

In alternative embodiments, an optional fourth portion may be cut at a fourth radius. In some embodiments, each of the first, second, third and optional fourth portions 320a-d may be cut at first, second, third and fourth radii relative to the longitudinal axis of elongated body 340. As illustrated in FIG. 7, compound barb 320 may include an arcuate first portion 320a which extends away from elongated body 340 at a first radius $r_2$, an arcuate second portion 320b which extends from first portion 320a at a second radius $r_3$, an arcuate third portion 320c which extends from second portion 320b at a third radius $r_4$, and an arcuate fourth portion 320d which extends from third portion 320c at a fourth radius $r_5$.

In other embodiments, a compound barb medical device may include an elongated body having a barb and first, second, and third portions being cut at first, second, and third angles respective to a longitudinal axis of the elongated body to form the barb.

The medical device in accordance with the present disclosure may be formed of the type selected from the group consisting of monofilament sutures, braided sutures, multi-filament sutures, surgical fibers, staples, anchors, slit sheets, ribbons, tape, mesh, stent, scaffolds, pledgets, vascular graft and ribbons. In an exemplary embodiment, the medical device is a suture. In another exemplary embodiment, the medical device is a staple.

The exemplary medical devices illustrated throughout the figures are shown to be elliptical in cross-sectional geometry. However, the cross-sectional geometry of the medical device may be of any suitable shape, for example, round, square, star shaped, octagonal, rectangular, polygonal and flat.

Figure 8:
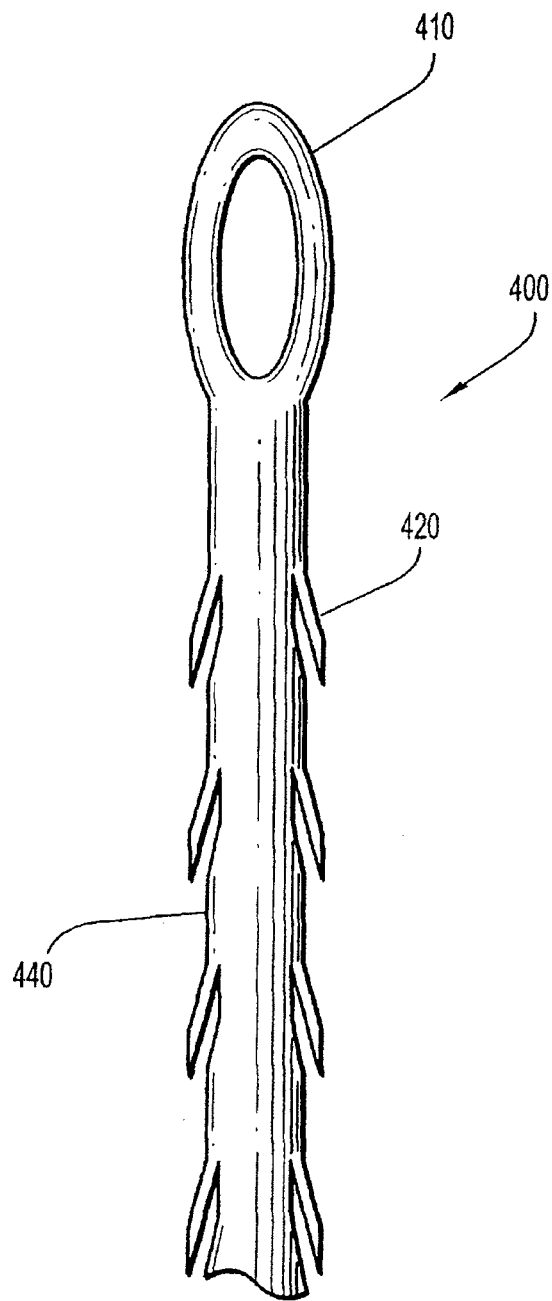
FIG. 8 is a plan view of a segment of a barbed suture having compound barbs and a loop formed at one end in accordance with the present disclosure.

In some embodiments, a loop is formed at the proximal end of the compound barb medical device which is configured to enhance retention of the medical device in body tissue at a desired position. As illustrated in FIG. 8, loop 410 is formed at the proximal end of the compound barb medical device 400. Loop 410 may be fixed at a predetermined location along the length of the elongated body 440 of the compound barb medical device 400. Loop 410 may be configured and dimensioned to be adjustable along the length of elongated body 440 (not shown).

In general, a method for forming a compound barb on a medical device includes the steps of providing a medical device, or a portion thereof, having a longitudinal axis and forming a compound barb along the medical device wherein the compound barb defines an inner surface which includes at least a first portion disposed at a first orientation relative to the longitudinal axis, a second portion disposed at a second orientation relative to the longitudinal axis, and optionally a third portion disposed at a third orientation relative to the longitudinal axis. In embodiments, at least one of the first, second, and third portions is substantially linear. In alternative embodiments, at least one of the first, second, and third portions is substantially non-linear or arcuate.

In embodiments, a method of forming a compound barb on a medical device includes forming a first cut in the medical device, the first cut having a first ratio of cut depth to diameter of the elongated body of the medical device; forming a second cut in the medical device, the second cut having a second ratio of cut depth to diameter of the elongated body of the medical device; and forming a third cut in the medical device, the third cut having a third ratio of cut depth to diameter of the elongated body of the medical device.

Figure 9:
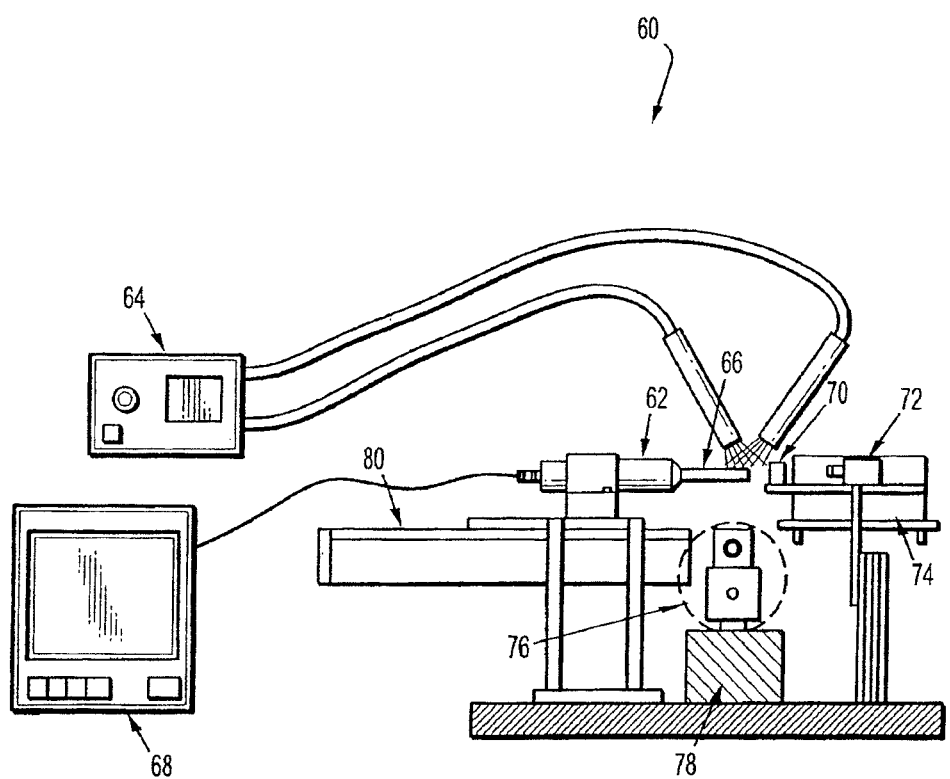
FIG. 9 is a schematic view of an embodiment of an apparatus and method of forming barbs on a medical device in accordance with the present disclosure.

FIG. 9 illustrates an embodiment of an apparatus and method of forming compound barbs in accordance with the present disclosure. The method is described, for example in U.S. patent application Ser. No. 12/178,361 filed Jul. 23, 2008 and titled "Method of Forming Barbs on a Suture", the entire disclosure of which is incorporated herein by reference. In the illustrative embodiment, ultrasonic energy is generated by an apparatus 60 that includes a converter 62 which transmits ultrasonic energy to a horn 66 that is operatively coupled to converter 62. Converter 62 converts electrical energy to mechanical energy which causes displacement of the tool at an ultrasonic frequency powered by an ultrasonic generator or booster 68. Booster 68 may be manipulated to either increase or decrease the ultrasonic frequency which may be transmitted to the tool. The ultrasonic frequency may range from about 1 kHz to about 100 kHz. In other embodiments, the ultrasonic frequency may range from about 10 kHz to about 90 kHz. In still further embodiments, the ultrasonic frequency may range from about 15 kHz to about 50 kHz. The ultrasonic signal amplitude may range from about 1μ to about 125μ. In other embodiments, the signal amplitude may range from about 15μ to about 60μ.

The ratio of the cut depth and the angle of the barbs relative to the elongated body of the medical device are variable based on the signal amplitude of ultrasonic energy applied to the cutting element. For example, as the ultrasonic amplitude is increased, the ratio of the cut depth to the diameter and the angle of the barbs are decreased. As the ultrasonic amplitude is decreased, the ratio of the cut depth to the diameter is increased, thereby increasing the angle of the barbs.

Referring back to FIG. 4A, in some embodiments, the compound barbs 12 as formed have a first angle α of approximately 0 degrees to about 90 degrees, in embodiments, from 30 degrees to 50 degrees between compound barb 12 and elongated body 14 and a first ratio of cut depth which is approximately 1% to about 40%, and in certain embodiments, about 10% to about 30% of the diameter of the body. Compound barb 12 as formed by the method of the present disclosure may have a second angle β of approximately 0 degrees to about 90 degrees, in embodiments, from 2 degrees to 25 degrees relative to the longitudinal axis with a second ratio of cut depth of approximately 5% to about 50%, and in certain embodiments, about 15% to about 45% of the diameter of elongated body 14. Compound barb 12 as formed by the method of the present disclosure may have a third angle γ of approximately 0 degrees to about 90 degrees, in embodiments, from about 25 degrees to about 50 degrees relative to the longitudinal axis with a third ratio of cut depth of approximately 15% to about 50%, and in some embodiments, from about 30% to about 50% the diameter of elongated body 14. In one embodiment, a plurality of barbs are formed at successive intervals along the longitudinal axis of the medical device.

With continued reference to FIG. 9, the apparatus 60 optionally includes a gripper such as anvil 70 for supporting a medical device. The gripper 70 supports the medical device at a fixed position. The horn 66 is configured and dimensioned to accept a cutting element such as a knife blade or a rotary blade (not shown) for forming the barbs on the medical device. The motorized slide 74 moves in an X, Y, and Z plane to allow the medical device to pass in front of the converter to form barbs thereon. Apparatus 60 also includes rotational motor 76 which rotates the medical device in a circular direction. Advance slide 78 moves the medical device after every cut a specified increment for the appropriate barb spacing. Apparatus 60 optionally includes camera 72 for recording the method of forming barbs and a light source 74 for optimizing the view of camera 72.

In embodiments, the medical device is moved to be in contact with the cutting element, or in other embodiments, the medical device is moved against the cutting element, at a specified first angle relative to the longitudinal axis of the elongated body of the medical device to form a first ratio of cut depth to diameter of approximately 1% to about 40%, in other embodiments a first ratio of cut depth to diameter of approximately 10% to about 30%. While the cutting element is still in contact with the medical device, a second angle is cut having a ratio of cut depth to diameter of approximately 5% to about 50%, in other embodiments a ratio of cut depth to diameter of approximately 15% to about 45%. Optionally, in other embodiments, while the cutting element is still in contact with the medical device, a third angle is cut having a ratio of cut depth to diameter of approximately 15% to about 50%, in other embodiments a ratio of cut depth to diameter of approximately 30% to about 50%.

The amount of time the blade is in contact with the medical device ranges, in embodiments, from about 1 millisecond to about 5 seconds. In other embodiments, the amount of time the blade is in contact with the medical device ranges from about 1 second to about 3 seconds. In still further embodiments, the amount of time the blade is in contact with the medical device is about 2 seconds.

In embodiments, the knife blade may be shaped substantially into a rectangle shape, a square shape, a circle shape, a flat shape, an octagonal shape, a triangle shape, a star shape, a spade shape, an arrow shape, a key shape and an elliptical shape. In some embodiments, the curvature of the knife blade is substantially concave or substantially convex.

In practice, the medical device passes in front of the converter 62 which includes the horn 66 and the anvil 70, then using ultrasonic energy at various frequencies and signal amplitudes cuts the material to a geometry. In embodiments, the medical device passes in front of converter 62 via motorized slide 74 which is configured and dimensioned to hold gripper 70 and camera 72 thereon. In certain embodiments, the medical device passes in front of converter 62, via a mechanical feeding mechanism with the medical device held tightly around two spools on each side of the apparatus (not shown). In other embodiments, the medical device passes in front of converter 62 via human manipulation of the medical device.

Still referring to FIG. 9, the apparatus 60 includes a converter 62 coupled to a horn 66 which operatively moves along a straight line X-Y plane via ultrasonic vibrational energy. The horn 66 includes a blade which contacts a surface of the medical device at an angle so as to form at least one barb on the medical device. The blade is appropriately positioned to contact the medical device via knife positioning slide 80. After each barb is formed, the medical device is moved in a linear motion on a X-Y plane via motorized slide 74 a specified length to allow another barb to be formed thereon. In embodiments, the medical device is moved in a X-Z plane via motorized slide 74 a specified length to form a barb thereon. In further embodiments, the medical device is moved in a Y-Z plane via motorized slide 74 a specified length to form a barb thereon. In alternative embodiments, the medical device is moved in a circular manner via rotational motor 76 to form a barb at a specified position. In embodiments, the medical device is moved in both a rotational and x-z plane rotation.

In practice, the barbs 12 are formed as either the knife blade or rotary blade (not shown) contacts the outer surface of the medical device. The blade may be urged into contact with the surface of the medical device, for example, by a reciprocating actuator in a straight line X-Y plane. It is contemplated, however, that in alternative embodiments, the blade may be held fixed and the medical device may be urged toward the blade. The blade makes contact with the surface of the medical device at an angle relative thereto such that the combined action of the movement of the blade into contact with the medical device surface and the ultrasonic vibration of the knife forms the desired barb. Advance slide 78 then moves the medical device after every cut a specified increment for the desired spacing of the barbs.

Ultrasonic energy may transfer heat to the medical device as it is forming the barbs thereon. Depending on the amplitude, the ultrasonic frequency may cause melting of medical device if the blades are left to penetrate medical device throughout the full wave cycle. To prevent this from occurring, in some embodiments, the application of ultrasonic energy is discontinued at some point prior to withdrawal of the blades from contact of the medical device. In other embodiments, this method may be used to vary the angle and the depth of the cut as indicated above with respect to the increase or decrease of the amplitude.

In some embodiments, barbs may be formed by making acute angular cuts directly into the elongated body of the medical device, with cut portions pushed outwardly and separated from the elongated body of the medical device. The depth of the barbs thus formed in the elongated body may depend on the diameter of the material and the depth of the cut.

In some embodiments, a suitable device for cutting a plurality of axially spaced barbs on the exterior of an elongated body of a medical device may use a gripper as a cutting bed, a cutting bed vise, a cutting template, and a converter and horn as the blade assembly to perform the cutting. In operation, the cutting device has the ability to produce a plurality of axially spaced barbs in the same or random configuration and at different angles in relation to each other.

In other embodiments, the barbs may be arranged on a first portion of a length of the elongated body of the medical device to allow movement of a first end of the medical device through tissue in one direction, while barbs on a second portion of the length of the elongated body of the medical device may be arranged to allow movement of the second end of the medical device in an opposite direction.

The barbs can be arranged in any suitable pattern, for example, helical, spiral, linear, or randomly spaced. The pattern may be symmetrical or asymmetrical. Barbs may be arranged around the entire circumference of an elongated body of a medical device, or a portion thereof. Further, barbs may be arranged over the entire length of an elongated body, or only through a portion or portions thereof. The number, configuration, spacing and surface area of the barbs can vary depending upon the tissue in which the medical device is used, as well as the composition and geometry of the material utilized to form the medical device. In embodiments, the barbs are positioned in a non-overlapping corkscrew-like pattern around the circumference of an elongated body. Additionally, the proportions of the barbs may remain relatively constant while the overall length of the barbs and the spacing of the barbs may be determined by the tissue being connected. For example, if the medical device is to be used to connect the edges of a wound in skin or tendon, the barbs may be made relatively short and more rigid to facilitate entry into this rather firm tissue. Alternatively, if the medical device is intended for use in fatty tissue, which is relatively soft, the barbs may be made longer and spaced further apart to increase the ability of the barbs to grip the soft tissue.

The surface area of the barbs can also vary. For example, fuller-tipped barbs can be made of varying sizes designed for specific surgical applications. For joining fat and relatively soft tissues, larger barbs may be desired, whereas smaller barbs may be more suitable for collagen-dense tissues. In some embodiments, a combination of large and small barbs within the same structure may be beneficial, for example when a suture is used in tissue repair with differing layer structures. In particular embodiments, a single directional suture may have both large and small barbs; in other embodiments a bi-directional suture may have both large and small barbs.

Medical device 100 in accordance with the present disclosure may be formed of absorbable materials, non-absorbable materials, and combinations thereof. More particularly, the medical device may be formed of an absorbable material selected from the group consisting of polyesters, polyorthoesters, polymer drugs, polydroxybutyrates, dioxanones, lactones, proteins, cat gut, collagens, carbonates, homopolymers thereof, copolymers thereof, and combinations thereof. In other embodiments, suitable absorbable materials which may be utilized to form the medical device include natural collagenous materials or synthetic resins including those derived from alkylene carbonates such as trimethylene carbonate, tetramethylene carbonate, and the like, caprolactone, glycolic acid, lactic acid, glycolide, lactide, homopolymers thereof, copolymers thereof, and combinations thereof. In some embodiments, glycolide and lactide based polyesters, especially copolymers of glycolide and lactide, may be utilized to form the medical device of the present disclosure. In other embodiments, a medical device of the present disclosure may be formed from dissolvable metals, such as magnesium.

In embodiments, suitable materials which may be utilized to form the medical devices in accordance with the present disclosure include homopolymers, copolymers, and/or blends possessing glycolic acid, lactic acid, glycolide, lactide, dioxanone, trimethylene caprolactone, and various combinations of the foregoing. For example, in some embodiments, a copolymer of glycolide and trimethylene carbonate may be utilized. Methods for forming such copolymers are within the purview of those skilled in the art and include, for example, the methods disclosed in U.S. Pat. Nos. 4,300,565 and 5,324,307, the entire disclosures of each or which are incorporated by reference herein. Suitable copolymers of glycolide and trimethylene carbonate may possess glycolide in amounts from about 60% to about 75% by weight of the copolymer, in embodiments, from about 65% to about 70% by weight of the copolymer, with the trimethylene carbonate being present in amounts from about 25% to about 40% by weight of the copolymer, in embodiments, from about 30% to about 35% by weight of the copolymer.

Other suitable materials include copolymers of lactide and glycolide, with lactide present in an amount from about 6% to about 12% by weight of the copolymer and glycolide being present in amounts from about 88% to about 94% by weight of the copolymer. In some embodiments, lactide is present from about 7% to about 11% by weight of the copolymer with glycolide being present in amounts from about 89% to about 98% by weight of the copolymer. In some other embodiments, lactide is present in an amount of about 9% by weight of the copolymer with the glycolide being present in an amount of about 91% by weight of the copolymer.

In embodiments, suitable materials for forming barbed medical devices according to the present disclosure include, in embodiments, copolymers of glycolide, dioxanone, and trimethylene carbonate. Such materials may include, for example, copolymers possessing glycolide in amounts from about 55% to about 65% by weight of the copolymer, in embodiments, from about 58% to about 62% by weight of the copolymer, in some embodiments, about 60% by weight of the copolymer; dioxanone in amounts from about 10% to about 18% by weight of the copolymer, in embodiments, from about 12% to about 16% by weight of the copolymer, in some embodiments about 14% by weight of the copolymer; and trimethylene carbonate in amounts from about 17% to about 35% by weight of the copolymer, in embodiments, from about 22% to about 30% by weight of the copolymer, in some embodiments, about 26% by weight of the copolymer.

Other suitable materials include a copolymer of glycolide, lactide, trimethylene carbonate, and ε-caprolactone may be utilized to form medical devices in accordance with the present disclosure. Such materials may include, for example, a random copolymer possessing caprolactone in amounts from about 14% to about 20% by weight of the copolymer, in embodiments, from about 16% to about 18% by weight of the copolymer, in some embodiments, about 17% by weight of the copolymer; lactide in amounts from about 4% to about 10% by weight of the copolymer, in embodiments, from about 6% to about 8% by weight of the copolymer, in some embodiments about 7% by weight of the copolymer; trimethylene carbonate in amounts from about 4% to about 10% by weight of the copolymer, in embodiments from about 6% to about 8% by weight of the copolymer, in some embodiments about 7% by weight of the copolymer; and glycolide in amounts from about 60% to about 78% by weight of the copolymer, in embodiments, from about 66% to about 72% by weight of the copolymer, in some embodiments about 69% by weight of the copolymer.

Barbed medical devices fabricated from an absorbable material in accordance with the present disclosure maintain their structural integrity after implantation (e.g., about 80% of original strength) for a period of time, depending on the various processing parameters and the particular copolymer used. Such characteristics include, for example, the components of the copolymer, including both the monomers utilized to form the copolymer and any additives thereto, as well as the processing conditions (e.g., rate of copolymerization reaction, temperature for reaction, pressure, etc.), and any further treatment of the resulting copolymers, i.e., coating, sterilization, etc.

The formation of barbs on an absorbable medical device may alter the degradation characteristics of the device. For example, the formation of barbs on a suture body may be utilized to alter the degradation time of a suture in accordance with the present disclosure as described in U.S. patent application Ser. No. 11/556,002 filed on Nov. 2, 2006 entitled "Long Term Bioabsorbable Barbed Sutures", the entire contents of which are incorporated by reference herein.

For non-absorbable barbed medical devices constructed in accordance with the present disclosure, suitable non-absorbable materials which may be utilized to form the medical device include polyolefins, such as polyethylene, polypropylene, copolymers of polyethylene and polypropylene, and blends of polyethylene and polypropylene; polyamides (such as nylon); polyamines; polyimines; polyesters such as polyethylene terephthalate; fluoropolymers such as polytetrafluoroethylene; polyether-esters such as polybutesters; polytetramethylene ether glycol; 1,4-butanediol; polyurethanes; and combinations thereof. The polypropylene can be isotactic polypropylene or a mixture of isotactic and syndiotactic or atactic polypropylene. In other embodiments, non-absorbable materials may include silk, cotton, linen, carbon fibers, and the like. In yet other embodiments, non-absorbable materials for forming a medical device of the present disclosure include metals, such as titanium, stainless steel and alloys thereof.

Filaments and fibers used for forming a medical device of the present disclosure may be formed using any technique within the purview of those skilled in the art, such as, for example, extrusion, molding and/or solvent casting.

In one embodiment, compound barbs are formed on a monofilament suture. A barbed monofilament suture may be used in embodiments where higher strength and longer absorption and strength profiles are desired. The compound barb monofilament sutures may be favored, for example, in dermal application where there is an increased risk of infection.

In some embodiments, medical devices of the present disclosure may include a yarn made of more than one filament, which may contain multiple filaments of the same or different materials. Where the medical devices are made of multiple filaments, the medical device can be made using any known technique such as, for example, braiding, weaving or knitting. The filaments may also be combined to produce a non-woven suture. The filaments themselves may be drawn, oriented, crinkled, twisted, comingled or air entangled to form yarns as part of the suture forming process.

Figure 12:
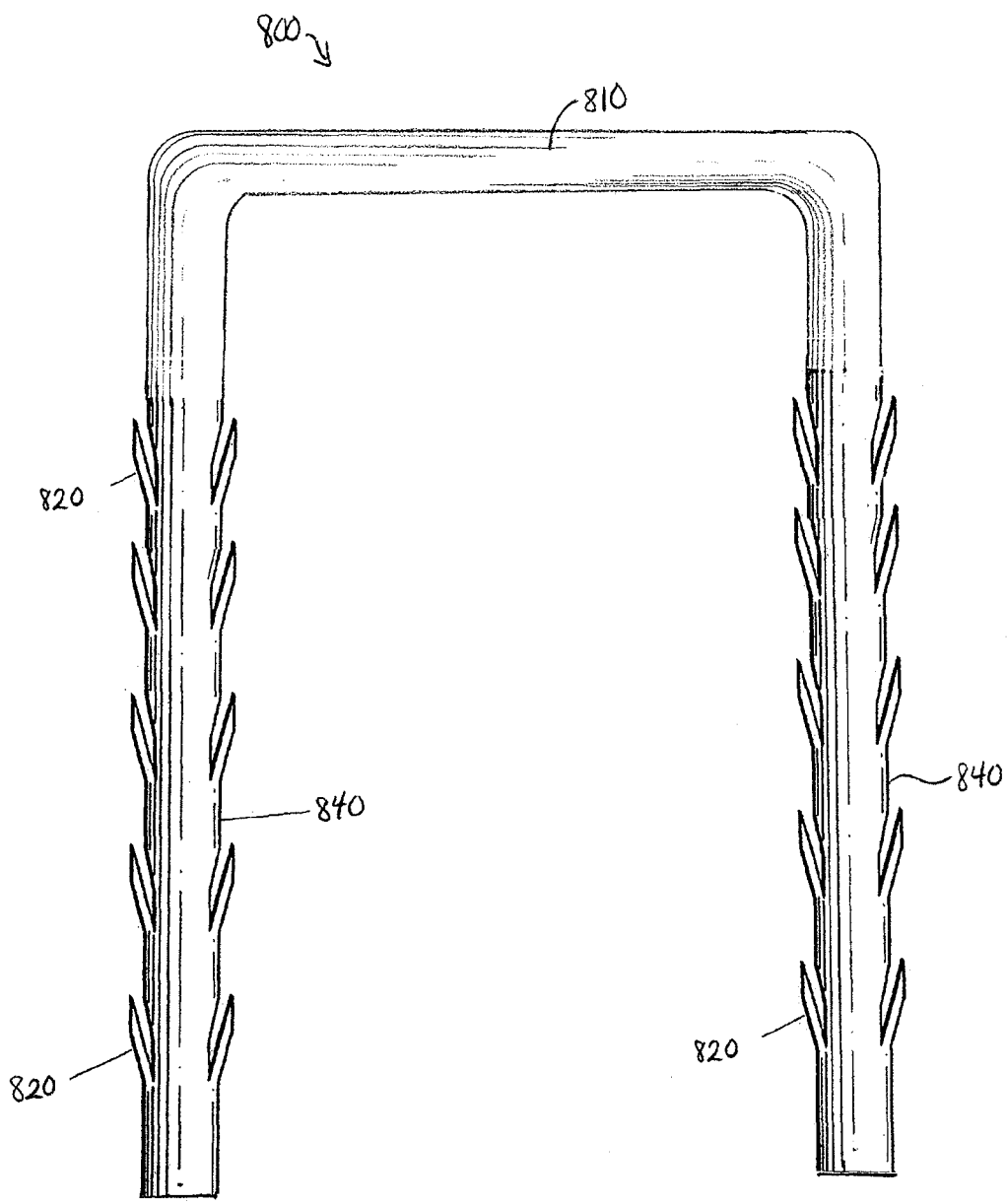
FIG. 12 is a plan view of a barbed staple having compound barbs formed in accordance with the present disclosure.

Barbs may be formed on staples in accordance with the present disclosure. As illustrated in FIG. 12, staple 800 include a crown 810 connecting a pair of elongated bodies or legs 840. The crown is shown as a straight member, but may be formed in any shape capable of interconnecting the legs 840, such as an apex. The legs 840 extend substantially perpendicular from the crown, but in alternate embodiments may extend from the crown at an angle therefrom. Barbs 820 are formed on legs 840. Barb angles, geometries, and methods for creating barbs include those referenced herein.

The staple 800 may be deployed and deformed into the typical crimped, "B" shape via a delivery device or alternatively, the barbs 820 of legs 840 can be deployed in the original configuration as shown in FIG. 12 because once deployed, the barbs 820 anchor into tissue thereby resisting deformation and enhancing the tissue pull-apart strength. The tissue pull-apart strength is dependent upon such factors as the angle of the barbs and the number of barbs per staple leg. The direction of the barbs also ensures that the staple will penetrate and properly anchor into tissue. Moreover, the diameter required of the staple to meet the holding strength is reduced compared to that of a typical unbarbed staple. Thus, the holding strength of the barbed staple can be made to match that of the crimped unbarbed staple, thereby eliminating the need for an anvil on the stapler and preventing the possibility of misfires, incomplete crimping, or overcrimping which may occur with conventional delivery devices.

In other embodiments, compound barb medical devices may include other medical devices such as braided sutures, surgical fibers, anchors, slit sheets, ribbons, tapes, meshes, stents, scaffolds, pledgets, and vascular grafts.

Once the medical device is barbed, it can be sterilized by any means within the purview of those skilled in the art.

In embodiments, the barbed medical device, in whole or in part (e.g., the medical device body, barbs, and/or portions thereof), may be constructed using shape memory polymers which are capable of adopting a shape in vivo suitable for adhering tissue, assisting in securing the barbed device, or affixing another surgical device, such as a mesh, to tissue. Shape memory polymeric materials utilized to form a barbed medical device of the present disclosure possess a permanent shape and a temporary shape. In embodiments, the temporary shape is of a configuration which enhances the ability of the surgeon to introduce the medical device into a patient's body. The permanent shape, which is assumed in vivo upon application of energy, such as heat or light, is of a configuration which enhances the retention of the medical device in tissue and/or adhesion of a surgical device to tissue.

Shape memory polymers are a class of polymers that, when formed into an object such as a suture or staple, can be temporarily deformed by mechanical force and then caused to revert back to an original shape when stimulated by energy. Shape memory polymers exhibit shape memory properties by virtue of at least two phase separated microdomains in their microstructure. The first domain is composed of hard, covalently cross-linked or otherwise chain motion-limiting structures, which act as anchors to retain the object's original shape. The second domain is a switchable soft structure, which can be deformed and then fixed to obtain a secondary or temporary shape.

In the case of heat stimulated shape memory polymers, a transition temperature ($T_{Trans}$) exists at which the shape change occurs during heating. The shape memory polymers can thus be tailored by altering material properties at the molecular level and by varying processing parameters. An object's primary shape may be formed with heat and pressure at a temperature at which the soft domains are flexible and the hard domains are not fully formed. The object may then be cooled so that the hard domains are more fully formed and the soft domains become rigid. The secondary or temporary shape can be formed by mechanically deforming the object, which is most readily accomplished at a temperature approaching or above $T_{Trans}$. Mechanical stresses introduced into the object are then locked into place by cooling the object to temperatures below $T_{Trans}$, so that the soft segments solidify to a rigid state. Once the object is heated to $T>T_{Trans}$, the soft segments soften and relax back to their original configuration and the object returns to its primary or original shape, sometimes referred to herein, as its permanent shape. The temperature at which a shape memory material reverts to its permanent shape may be referred to, in embodiments, as its permanent temperature ($T_{perm}$).

Polymers possessing shape memory properties which may be used to construct barbed medical devices disclosed herein include, for example, synthetic materials, natural materials (e.g., biological) and combinations thereof, which may be biodegradable and/or non-biodegradable. As used herein, the term "biodegradable" includes both bioabsorbable and bioresorbable materials. By biodegradable, it is meant that the materials decompose, or lose structural integrity under body conditions (e.g., enzymatic degradation, hydrolysis) or are broken down (physically or chemically) under physiologic conditions in the body (e.g., dissolution) such that the degradation products are excretable or absorbable by the body.

Suitable non-degradable materials which may possess shape memory properties include, but are not limited to, polyolefins such as polyethylene (including ultra high molecular weight polyethylene) and polypropylene including atactic, isotactic, syndiotactic, and blends thereof; polyethylene glycols; polyethylene oxides; ultra high molecular weight polyethylene; copolymers of polyethylene and polypropylene; polyisobutylene and ethylene-alpha olefin copolymers; fluorinated polyolefins such as fluoroethylenes, fluoropropylenes, fluoroPEGs, and polytetrafluoroethylene; polyamides such as nylon, Nylon 6, Nylon 6,6, Nylon 6,10, Nylon 11, Nylon 12, and polycaprolactam; polyamines; polyimines; polyesters such as polyethylene terephthalate, polyethylene naphthalate, polytrimethylene terephthalate, and polybutylene terephthalate; polyethers; polytetramethylene ether glycol; polybutesters, including copolymers of butylene terephthalate and polytetramethylene ether glycol; 1,4-butanediol; polyurethanes; acrylic polymers; methacrylics; vinyl halide polymers and copolymers such as polyvinyl chloride; polyvinyl alcohols; polyvinyl ethers such as polyvinyl methyl ether; polyvinylidene halides such as polyvinylidene fluoride and polyvinylidene chloride; polychlorofluoroethylene; polyacrylonitrile; polyaryletherketones; polyvinyl ketones; polyvinyl aromatics such as polystyrene; polyvinyl esters such as polyvinyl acetate; copolymers of vinyl monomers with each other and olefins such as ethylene-methyl methacrylate copolymers; acrylonitrile-styrene copolymers; ABS resins; ethylene-vinyl acetate copolymers; alkyd resins; polycarbonates; polyoxymethylenes; polyphosphazine; polyimides; epoxy resins; aramids; rayon; rayon-triacetate; spandex; silicones; and copolymers and combinations thereof. Additionally, non-biodegradable polymers and monomers may be combined with each other.

Suitable bioabsorbable polymers which may possess shape memory properties include, but are not limited to, aliphatic polyesters; polyamides; polyamines; polyalkylene oxalates; poly(anhydrides); polyamidoesters; copoly(ether-esters); poly(carbonates) including tyrosine derived carbonates; poly (hydroxyalkanoates) such as poly(hydroxybutyric acid), poly (hydroxyvaleric acid), and poly(hydroxybutyrate); polyimide carbonates; poly(imino carbonates) such as poly (bisphenol A-iminocarbonate and the like); polyorthoesters; polyoxaesters including those containing amine groups; polyphosphazenes; poly(propylene fumarates); polyurethanes; polymer drugs such as polydiflunisol, polyaspirin, and protein therapeutics; biologically modified (e.g., protein, peptide) bioabsorbable polymers; and copolymers, block copolymers, homopolymers, blends, and combinations thereof.

Suitable aliphatic polyesters may include, but are not limited to, homopolymers and copolymers of lactide (including lactic acid, D-, L- and meso lactide); glycolide (including glycolic acid); epsilon-caprolactone; p-dioxanone (1,4-dioxan-2-one); trimethylene carbonate (1,3-dioxan-2-one); alkyl derivatives of trimethylene carbonate; Δ-valerolactone; β-butyrolactone; γ-butyrolactone; ε-decalactone; hydroxybutyrate; hydroxyvalerate; 1,4-dioxepan-2-one (including its dimer 1,5,8,12-tetraoxacyclotetradecane-7,14-dione); 1,5-dioxepan-2-one; 6,6-dimethyl-1,4-dioxan-2-one; 2,5-diketomorpholine; pivalolactone; α,αdiethylpropiolactone; ethylene carbonate; ethylene oxalate; 3-methyl-1,4-dioxane-2,5-dione; 3,3-diethyl-1,4-dioxan-2,5-dione; 6,8-dioxabicycloctane-7-one; and polymer blends and copolymers thereof.

Other suitable biodegradable polymers include, but are not limited to, poly(amino acids) including proteins such as collagen (I, II and III), elastin, fibrin, fibrinogen, silk, and albumin; peptides including sequences for laminin and fibronectin (RGD); polysaccharides such as hyaluronic acid (HA), dextran, alginate, chitin, chitosan, and cellulose; glycosaminoglycan; gut; and combinations thereof. Collagen as used herein includes natural collagen such as animal derived collagen, gelatinized collagen, or synthetic collagen such as human or bacterial recombinant collagen.

Additionally, synthetically modified natural polymers such as cellulose and polysaccharide derivatives, including alkyl celluloses, hydroxyalkyl celluloses, cellulose ethers, cellulose esters, nitrocelluloses, and chitosan may be utilized. Examples of suitable cellulose derivatives include methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxymethyl cellulose (CMC), cellulose triacetate, and cellulose sulfate sodium salt. These may be collectively referred to herein, in embodiments, as "celluloses."

In embodiments, combinations of both degradable and non-degradable materials, including those having shape memory characteristics, may be utilized.

In embodiments, the shape memory polymer may be a copolymer of two components with different thermal characteristics, such as oligo (epsilon-caprolactone) dimethacrylates and butyl acrylates, including poly(epsilon-caprolactone) dimethacrylate-poly(n-butyl acrylate), or a diol ester and an ether-ester diol such as oligo (epsilon caprolactone) diol/oligo (p-dioxanone) diol copolymers. These multi-block oligo (epsilon-caprolactone) diol/oligo (p-dioxanone) diol copolymers possess two block segments: a "hard" segment and a "switching" segment linked together in linear chains. Such materials are disclosed, for example, in Lendlein, "Shape Memory Polymers-Biodegradable Sutures," Materials World, Vol. 10, no. 7, pp. 29-30 (July 2002), the entire disclosure of which is incorporated by reference herein.

In other embodiments, blends of bioabsorbable materials may be utilized including, but not limited to, urethanes blended with lactic acid and/or glycolic acid, homopolymers thereof or copolymers thereof, and acrylates blended with caprolactones such as polycaprolactone dimethacrylate poly (butyl acrylate) blends, and combinations thereof.

Other examples of suitable shape memory polymers and means for forming permanent and temporary shapes therewith are set forth in Lendlein et al., "Shape memory polymers as stimuli-sensitive implant materials," Clinical Hemorheology and Microcirculation, 32 (2005) 105-116, Lendlein et al., "Biodegradable, Elastic Shape memory Polymers for Potential Biomedical Applications," Science, Vol. 269 (2002) 1673-1676, and Lendlein et al., "Shape-Memory Polymers," Angew. Chem. Int. Ed., 41 (2002) 2035-2057, the entire disclosures of each of which are incorporated by reference herein.

Table 1 below further illustrates compositions which demonstrate shape memory effects. The block copolymers of each composition are in annealed wire format, the proposed soft and hard segments, and the glass transition temperature ($T_g$), having been measured by differential scanning calorimetry which is equal to $T_{Trans}$.

TABLE 1

| Composition (mol %) | Soft Domain | Hard Domain | $T_g$ ($T_{Trans}$) [° C.] |
|---|---|---|---|
| 15% Polydioxanone 85% Poly (L-lactide) | Polydioxanone and Amorphous Polylactide | Crystalline Polylactide | 54 |
| 20% Polydioxanone 80% Poly (L-lactide) | Polydioxanone and Amorphous Polylactide | Crystalline Polylactide | 45 |
| 15% Trimethylene Carbonate 85% Poly (L-lactide) | Trimethylene Carbonate and Amorphous Polylactide | Crystalline Polylactide | 54 |
| 20% Trimethylene Carbonate 80% Poly (L-lactide) | Trimethylene Carbonate and Amorphous Polylactide | Crystalline Polylactide | 55 |

The copolymers in Table 1 may undergo a partial shift when approaching $T_g$ and $T_{Trans}$ may be depressed when the materials are in aqueous solution. Since these polymers degrade by water absorption and bulk hydrolysis, water molecules entering the polymer matrices may act as plasticizers, causing the soft segments to soften at lower temperatures than in dry air. Thus, polymers exhibiting $T_{Trans}$ depression in aqueous solution may maintain a temporary shape through temperature excursions in the dry state, such as during shipping and storage, and shape shift to its permanent shape at body temperatures upon implantation.

Thus, in embodiments, the shape memory polymer may include a block copolymer of polydioxanone and polylactide with the polydioxanone present in an amount from about 5 mol % to about 20 mol % of the copolymer, in embodiments from about 15 mol % to about 19 mol % of the copolymer, and the polylactide present in an amount from about 80 mol % to about 95 mol % of the copolymer, in embodiments from about 81 mol % to about 85 mol % of the copolymer. In other embodiments, the shape memory polymer may include a block copolymer of trimethylene carbonate and polylactide, with the trimethylene carbonate present in an amount from about 5 mol % to about 20 mol % of the copolymer, in embodiments from about 15 mol % to about 19 mol % of the copolymer, and the polylactide may be present in an amount from about 80 mol % to about 95 mol % of the copolymer, in embodiments from about 81 mol % to about 85 mol % of the copolymer.

It is envisioned that $T_{Trans}$ may be tailored by changing block segment molar ratios, polymer molecular weight, and time allowed for hard segment formation. In embodiments, $T_{Trans}$ may be tailored by blending various amounts of low molecular weight oligomers of the soft segment domain into the copolymer. Such oligomers may segregate to soft domains and act as plasticizers to cause a downward shift in $T_{Trans}$.

Additionally, the copolymers forming the barbed medical devices of the present disclosure may include emulsifying agents, solubilizing agents, wetting agents, taste modifying agents, plasticizers, active agents, water soluble inert fillers, preservatives, buffering agents, coloring agents, and stabilizers. Addition of a plasticizer to the formulation can improve flexibility. The plasticizer or mixture of plasticizers may be polyethylene glycol, glycerol, sorbitol, sucrose, corn syrup, fructose, dioctyl-sodium sulfosuccinate, triethyl citrate, tributyl citrate, 1,2-propylenglycol, mono-, di- or triacetates of glycerol, or natural gums.

In some embodiments, crystalline degradable salts or minerals may be added to the block copolymer compositions to create polymer composites which may improve shape memory properties. An example of such a composite using polylactide homopolymer and crystalline hydroxyapatite is described in Zheng et al., "Shape memory properties of poly (D,L-lactide/hydroxyapatite composites," Biomaterials, 27 (2006) 4288-4295, the entire disclosure of which is incorporated by reference herein.

Other shape memory materials, including shape memory metals and metal alloys such as Nitinol, may also be used to form the medical devices of the present disclosure.

In embodiments, a molding process may be utilized to produce a barbed medical device in accordance with the present disclosure. Plastic molding methods are within the purview of those skilled in the art and include, but are not limited to, melt molding, solution molding, and the like. Injection molding, extrusion molding, compression molding and other methods can also be used as the melt molding technique. Once placed in the mold with the proper dimensions and configuration, the polymeric material used to form the medical device may be heated to a suitable temperature, such as the permanent temperature ($T_{perm}$) which may, in embodiments, be the melting temperature of the shape memory polymeric material utilized to form the medical device. Heating of the medical device may be at suitable temperatures including, for example, from about 40° C. to about 180° C., in embodiments from about 80° C. to about 150° C., for a period of time of from about 2 minutes to about 60 minutes, in embodiments from about 15 minutes to about 20 minutes, to obtain the permanent shape and dimensions.

The temperature for deformation treatment of the medical device molded with a previously memorized shape is one that makes possible ready deformation without producing cracks and should not exceed the temperature adopted for the shape memorization (e.g., $T_{perm}$). Deformation treatment at a temperature exceeding that for the original shape memorization may cause the object to memorize/program a new deformed shape.

After the medical device with the desired shape has been formed, the medical device may be deformed above $T_{trans}$ to obtain an alternate, temporary shape. Suitable temperatures for deformation will vary depending on the shape memory polymer utilized, but generally may be above the transition temperature of the polymer ($T_{trans}$) but below the $T_{perm}$. In embodiments, the shape memory polymer may be cooled from its $T_{perm}$ to a lower temperature which remains above the $T_{trans}$ and deformed, in embodiments by hand and/or mechanical means. In other embodiments, the medical device may be deformed at room temperature (about 20° C. to about 25° C.) to obtain its temporary shape, although the temperature may differ depending upon the particular polymer employed. The medical device may then be cooled to a temperature below the $T_{trans}$ of the material utilized to form the medical device, at which time the medical device of the present disclosure is ready for use. As the $T_{trans}$ is usually greater than room temperature, in embodiments cooling to room temperature may be sufficient to lock in the temporary shape.

There are no particular limitations on the manner in which the deformation can be achieved. Deformation can be achieved either by hand or by means of a suitable device selected to provide the desired temporary configuration to the medical device.

In order to keep the shape of the medical device in its temporary shape, the shape memory barbed medical device of the present disclosure should be stored at a temperature which will not cause a transition to the permanent shape. In embodiments, the shape memory medical device may be stored in a refrigerator.

In embodiments, the shape memory polymeric materials of the present disclosure may be compressed or expanded into temporary forms that are smaller or larger in diameter than their permanent shape.

The medical devices thus prepared recover their permanent shape upon application of energy, such as on heating, either by placement in a patient's body, or the addition of exogenous heat at a prescribed temperature, in embodiments above the $T_{trans}$ of the shape memory polymer utilized. As the medical devices of the present disclosure are utilized in a living body, heating with body heat (about 37° C.) is possible. In such a case, the temperature for shape programming should be as low as possible and the recovery of the permanent may occur fairly slowly. In embodiments, recovery of the permanent shape may occur from about 1 second to about 5 seconds after insertion into tissue.

In embodiments, the shape memory polymer medical device is a barbed suture as described above. The suture may be barbed and then annealed near its crystallization temperature to program a permanent shape to the suture and/or its barbs. For example, the permanent shape of the suture may include the barbs extending away from the elongated body. A temporary shape may then be imparted to the suture. For example, the barbed suture may be fed through a tube having an inner diameter sufficiently small to compress the barbs against the suture body. The tube may then be heated above the transition temperature of the shape memory polymeric material to soften the barbs, and then the tube and suture may be cooled to set the temporary shape. The suture may then be removed from the tube with the barbs approximated, or in alignment, with the elongated body. After deployment in the body, the barbs will extend back to their primary extended shape, thereby limiting movement of the suture within tissue. In other embodiments, the shape memory medical device may be a barbed staple as also described above.

However, in some embodiments a higher shape memory temperature may be desirable in order to make the shape recover at a slightly higher temperature than body temperature. Thus, in some cases, releasing the medical device from deformation to recover the permanent shape can be achieved by heating. On heating at a temperature of from about 30° C. to about 50° C., in embodiments from about 39° C. to about 43° C., the temporary shape may be released and the permanent shape recovered. The higher the temperature for heating, the shorter the time required for recovery of the permanent shape. The means for this heating is not limited. Heating can be accomplished by using a gas or liquid heating medium, heating devices, ultrasonic waves, electrical induction, and the like. Of course, in an application involving a living body, care must be taken to utilize a heating temperature which will not cause burns. Examples of liquid heating media include, physiological saline solution, alcohol, combinations thereof, and the like.

Similarly, in other embodiments, electrically active polymers, also known as electroactive polymers, which can alter their configuration upon application of electricity, may be utilized to fashion medical devices in accordance with the present disclosure. Suitable examples of electroactive polymers include poly(aniline), substituted poly(aniline)s, polycarbazoles, substituted polycarbazoles, polyindoles, poly(pyrrole)s, substituted poly(pyrrole)s, poly(thiophene)s, substituted poly(thiophene)s, poly(acetylene)s, poly(ethylene dioxythiophene)s, poly(ethylenedioxypyrrole)s, poly(p-phenylene vinylene)s, and the like, or combinations including at least one of the foregoing electroactive polymers. Blends or copolymers or composites of the foregoing electroactive polymers may also be used.

Similar to the change in shape which a shape memory material may undergo upon the application of energy, such as heat, in embodiments an electroactive polymer may undergo a change in shape upon the application of electricity from a low voltage electrical source (such as a battery). Suitable amounts of electricity which may be applied to effect such change will vary with the electroactive polymer utilized, but can be from about 5 volts to about 30 volts, in embodiments from about 10 volts to about 20 volts. The application of electricity will result in the medical device constructed of the electroactive polymer changing its shape from a temporary shape to its permanent shape.

While an electroactive polymer does not have the same permanent shape and temporary shape as those terms are described above with respect to shape memory polymers, as used herein the term "permanent shape" as applied to an electroactive polymer means, in embodiments, the shape the electroactive polymer adopts upon the application of electricity, and the term "temporary shape" as applied to an electroactive polymer means, in embodiments, the shape of the electroactive polymer adopts in the absence of electricity.

In some embodiments, the sutures may include metals (e.g. steel and degradable magnesium), metal alloys or the like.

As used herein, the terms "fibers", "filaments" and "yarns" each may be used to construct sutures or other devices, in whole or in part. The term "fibers," in this context, are generally used to designate natural or synthetic structures that have a length approximately 3 orders of magnitude greater than their diameter or width. The term "filaments" are typically used to describe "fibers" of indefinite or extreme length, and "yarns" as a generic term for a continuous strand of twisted or untwisted "fibers" or "filaments" in a form suitable for knitting, weaving, braiding or otherwise intertwining.

In embodiments, sutures of the present disclosure may possess a core/sheath configuration, fibers may possess a core/sheath configuration, yarns may possess a core/sheath configuration, or both. Any material described herein, including the shape memory materials described above, may be utilized to form the core, the sheath, or both.

Sutures of the present disclosure may be monofilament or multifilament (e.g. braided). Methods for making sutures from these suitable materials are within the purview of those skilled in the art (e.g. extrusion and molding). The filaments may be combined to create a multifilament suture using any technique within the purview of one skilled in the art such as comingling, twisting, braiding, weaving, entangling, and knitting. For example, filaments may be combined to form a yarn or they may be braided. In another example, filaments may be combined to form a yarn and then those multifilament yarns may be braided. Those skilled in the art reading this disclosure will envision other ways in which filaments may be combined. Fibers may also be combined to produce a nonwoven multifilament large diameter suture. In certain embodiments, a multifilament structure useful in forming a device according to the present disclosure may be produced by braiding. The braiding can be done by any method within the purview of those skilled in the art. For example, braid constructions for sutures and other medical devices are described in U.S. Pat. Nos. 5,019,093; 5,059,213; 5,133,738; 5,181,923; 5,226,912; 5,261,886; 5,306,289; 5,318,575; 5,370,031; 5,383,387; 5,662,682; 5,667,528; and 6,203,564; the entire disclosures of each of which are incorporated by reference herein. Furthermore, the device of the present disclosure may include portions which are monofilament and portions which are multifilament. In some embodiments, the proximal end of the elongate body may be a multifilament and the looped portion (loop portion described below) may be a monofilament.

Medical devices in accordance with the present disclosure may be coated or impregnated with one or more synthetic or natural polymers e.g., bioactive agents which accelerate or beneficially modify the healing process when the medical device is applied to a wound or surgical site. In certain embodiments, the coating may be formed from absorbable polymers selected from the group consisting of lactones, carbonates, polyorthoesters, hydroxyalkoanates, hydroxybutyrates, bioactive agents, polyanhydrides, silicone, vinyl polymers, high molecular weight waxes and oils, natural polymers, proteins, polysaccharides, suspendable particulates, dispersible particulates, microspheres, nanospheres, rods, homopolymers thereof, copolymers thereof, and combinations thereof.

Suitable bioactive agents include, for example, biocidal agents, antimicrobial agents, antibiotics, anti-proliferatives, medicants, growth factors, anti-clotting agents, clotting agents, analgesics, anesthetics, anti-inflammatory agents, wound repair agents and the like, chemotherapeutics, biologics, protein therapeutics, monoclonal or polyclonal antibodies, DNA, RNA, peptides, polysaccharides, lectins, lipids, probiotics, diagnostic agents, angiogenics, anti-angiogenic drugs, polymeric drugs, and combinations thereof.

Bioactive agents include substances which are beneficial to the animal and tend to promote the healing process. For example, a suture can be provided with a bioactive agent that will be deposited at the sutured site. The bioactive agent can be chosen for its antimicrobial properties, capability for promoting wound repair and/or tissue growth, or for specific indications such as thrombosis. In embodiments, combinations of such agents may be applied to the medical device of the present disclosure after formation of the barbs.

The term "antimicrobial agent" as used herein includes an agent which by itself or through the assistance of the immune system, helps the body destroy or resist microorganisms which may be pathogenic. An antimicrobial agent includes antibiotics, antiseptics, quorum sensing blockers, antifungals, anti-virals, surfactants, metal ions, antimicrobial proteins and peptides, antimicrobial polysaccharides, disinfectants and combinations thereof. Antimicrobial agents which are slowly released into the tissue can be applied in this manner to aid in combating clinical and sub-clinical infections in a surgical or trauma wound site. In embodiments, suitable antimicrobial agents may be soluble in one or more solvents.

In embodiments, the following anti-microbial agents may be used alone or in combination with other bioactive agents described herein: an anthracycline, doxorubicin, mitoxantrone, a fluoropyrimidine, 5-fluorouracil (5-FU), a folic acid antagonist, methotrexate, mitoxantrone, quorum sensing blocker, brominated or halogenated furanones, a podophylotoxin, etoposide, camptothecin, a hydroxyurea, a platinum complex, cisplatin, doxycycline, metronidazole, trimethoprim-sulfamethoxazole, rifamycins like rifampin, a fourth generation penicillin (e.g., a ureidopenicillin a carboxypenicillin, meziocillin, piperacillin, carbenicillin, and ticarcillin, and an analogue or derivative thereof), a first generation cephalosporin (e.g., cephazolin sodium, cephalexin, cefazolin, cephapirin, and cephalothin), a carboxypenicillin (e.g., ticarcillin), a second generation cephalosporin (e.g., cefuroxime, cefotetan, and cefoxitin), a third generation cephalosporin (e.g., naxcel, cefdinir, cefoperazone, ceftazidime, ceftriaxone, and cefotaxime), polyvinyl pyrrolidone (PVP), a fourth generation cephalosporin (e.g., cefepime), a monobactam (e.g., aztreonam), a carbapenem (e.g., imipenem, ertapenem and meropenem), an aminoglycoside (e.g., streptomycin, gentamicin, tobramycin, and amikacin), an MSL group member (e.g., a macrolide, a long acting macrolide, a lincosamide, a streptogramin, Erythromycin, Azithromycin, Clindamycin, Syneroid, clarithromycin, and kanamycin sulfate), tetracyclines (e.g., minocycline, fusidic acid, trimethoprim, metronidazole), a quinolone (e.g., ciprofloxacin, ofloxacin, gatifloxacin, moxifloxacin, levofloxacin, and trovafloxacin), a DNA synthesis inhibitor (e.g., metronidazole), a sulfonamide (e.g. sulfamethoxazole, trimethoprim, including cefixime, spectinomycin, tetracycline, nitrofurantoin, polymyxin B, and neomycin sulfate), beta-lactam inhibitors like sulbactam, chloramphenicol, glycopeptides like vancomycin, mupirocin, polyenes like amphotericin B, azoles like fluconazole, and other known antimicrobial agents known in the art.

Examples of chemotherapeutics which may be utilized include one or more of the following: doxorubicin (Dox), paclitaxel (PTX), camptothecin (CPT), polyglutamate-PTX (CT-2103 or Xyotax), N-(2-hydroxypropyl)methacrylamide (HPMA) copolymer, anthracycline, mitoxantrone, letrozole, anastrozole, epidermal growth factor receptor inhibitors, tyrosine kinase inhibitors, modulators of apoptosis, anthracycline antibiotics such as daunorubicin and doxorubicin, alkylating agents such as cyclophosphamide and melphalan, antimetabolites such as methotrexate and 5-fluorouracil, poly (ethylene glycol) (PEG), poly(glutamic acid) (PGA), polysaccharides, monoclonal antibody and polymer-drug conjugates thereof, copolymers thereof and combinations thereof.

Clotting agents which may be incorporated into a medical device of the present disclosure include one or more of the following: a fibrosing agent that promotes cell regeneration, a fibrosing agent that promotes angiogenesis, a fibrosing agent that promotes fibroblast migration, a fibrosing agent that promotes fibroblast proliferation, a fibrosing agent that promotes deposition of extracellular matrix, a fibrosing agent that promotes tissue remodeling, a fibrosing agent that is a diverticular wall irritant, silk (such as silkworm silk, spider silk, recombinant silk, raw silk, hydrolyzed silk, acid-treated silk, and acylated silk), talc, chitosan, bleomycin or an analogue or derivative thereof, connective tissue growth factor (CTGF), metallic beryllium or an oxide thereof, copper, saracin, silica, crystalline silicates, quartz dust, talcum powder, ethanol, a component of extracellular matrix, oxidized cellulose, polysaccharides, collagen, fibrin, fibrinogen, poly(ethylene terephthalate), poly(ethylene-co-vinylacetate), N-carboxybutylchitosan, an RGD protein, a polymer of vinyl chloride, cyanoacrylate, crosslinked poly(ethylene glycol)-methylated collagen, an inflammatory cytokine, TGFβ, PDGF, VEGF, TNFα, NGF, GM-CSF, IGF-a, IL-1, IL-8, IL-6, a growth hormone, a bone morphogenic protein, a cell proliferative agent, dexamethasone, isotretinoin, 17-β-estradiol, estradiol, diethylstibesterol, cyclosporine a, all-trans retinoic acid or an analogue or derivative thereof, wool (including animal wool, wood wool, and mineral wool), cotton, bFGF, polyurethane, polytetrafluoroethylene, activin, angiopoietin, insulin-like growth factor (IGF), hepatocyte growth factor (HGF), a colony-stimulating factor (CSF), erythropoietin, an interferon, endothelin-1, angiotensin II, bromocriptine, methylsergide, fibrosin, fibrin, an adhesive glycoprotein, proteoglycan, hyaluronan, secreted protein acidic and rich in cysteine (SPaRC), a thrombospondin, tenacin, a cell adhesion molecule, dextran based particles, an inhibitor of matrix metalloproteinase, magainin, tissue or kidney plasminogen activator, a tissue inhibitor of matrix metalloproteinase, carbon tetrachloride, thioacetamide, superoxide dismutase to scavenge tissue-damaging free radicals, tumor necrosis factor for cancer therapy, colony stimulating factor, interferon, interleukin-2 or other lymphokines to enhance the immune system, platelet rich plasma, thrombin, peptides such as self assembly peptide systems, amino acids such as radA based amino acids, hydrogels such as super absorbing hydrogel materials, combinations thereof, and so forth.

A wide variety of anti-angiogenic factors may be readily utilized within the context of the present disclosure. Representative examples include Anti-Invasive Factor; retinoic acid and derivatives thereof; paclitaxel a highly derivatized diterpenoid; Suramin; Tissue Inhibitor of Metalloproteinase-1; Tissue Inhibitor of Metalloproteinase-2; Plasminogen Activator Inhibitor-1; Plasminogen Activator Inhibitor-2; various forms of the lighter "d group" transition metals such as, for example, vanadium, molybdenum, tungsten, titanium, niobium, and tantalum species and complexes thereof; Platelet Factor 4; Protamine Sulphate (Clupeine); Sulphated Chitin Derivatives (prepared from queen crab shells); Sulphated Polysaccharide Peptidoglycan Complex (SP-PG) (the function of this compound may be enhanced by the presence of steroids such as estrogen, and tamoxifen citrate); Staurosporine; Modulators of Matrix Metabolism, including for example, proline analogs (L-azetidine-2-carboxylic acid (LACA), cishydroxyproline, d,L-3,4-dehydroproline, Thiaproline, $\alpha,\alpha$-dipyridyl, and $\beta$-aminopropionitrile fumarate); MDL 27032 (4-propyl-5-(4-pyridinyl)-2(3H)-oxazolone; Methotrexate; Mitoxantrone; Heparin; Interferons; 2 Macroglobulin-serum; ChIMP-3; Chymostatin; $\beta$-Cyclodextrin Tetradecasulfate; Eponemycin; Camptothecin; Fumagillin Gold Sodium Thiomalate ("GST"); D-Penicillamine ("CDPT"); $\beta$-1-anticollagenase-serum; $\alpha$2-antiplasmin; Bisantrene; Lobenzarit disodium (N-(2)-carboxyphenyl-4-chloroanthronilic acid disodium or "CCA"; Thalidomide; Angostatic steroid; AGM-1470; carboxynaminolmidazole; metalloproteinase inhibitors such as BB94; analogues and derivatives thereof, and combinations thereof.

A wide variety of polymeric drugs may be readily utilized within the context of the present disclosure. Representative examples include steroidal anti-inflammatory agents, non-steroidal anti-inflammatory agents, and combinations thereof. Examples of the non-steroidal anti-inflammatory agent which may be used with the present disclosure are aspirin, indomethacin, ibuprofen, phenylbutazone, diflusinal, and combinations thereof.

Examples of the steroidal anti-inflammatory agent which may be used are glucocorticoids such as cortisone and hydrocortisone, betamethasone, dexamethasone, fluprednisolone, prednisone, methylprednisolone, prednisolone, triamcinolone, paramethasone, and combinations thereof.

Although the above bioactive agents have been provided for the purposes of illustration, it should be understood that the present disclosure is not so limited. In particular, although certain bioactive agents are specifically referred to above, the present disclosure should be understood to include analogues, derivatives and conjugates of such agents. Moreover, while the above disclosure refers to the placement of bioactive agents in coatings, such bioactive agents may be combined with any material utilized to form any portion of a medical device, utilizing means within the purview of those skilled in the art. Thus, for example, a bioactive agent may be part of a polymeric material, or combined with a polymeric material, utilized to form any portion of a barbed device of the present disclosure.

Medical devices in accordance with this disclosure can also include, for example, biologically acceptable plasticizers, antioxidants and colorants, which can be impregnated into the filament(s) utilized to form a suture of the present disclosure or included in a coating on a medical device of the present disclosure.

Bioactive agents may be applied onto a barbed medical device of the present disclosure utilizing any method within the purview of one skilled in the art including, for example, dipping, spraying, vapor deposition, brushing, mixing, compounding and the like. In embodiments, a bioactive agent may be deposited within the barb angles, that is, the angle formed between the barb and the medical device surface in accordance with the present disclosure as described in U.S. patent application Ser. No. 11/899,852 filed on Sep. 6, 2007 entitled "Bioactive Substance in a Barbed Suture", the entire contents of which are incorporated by reference herein. In embodiments, the bioactive agent may be deposited on any barbed and/or un-barbed portion of the medical device, such as, for example, on at least a portion of the legs of a staple and/or the crown connecting the legs.

Medical devices of the present disclosure may contain additives such as dyes, pigments, and colorants in order to increase the visibility of the device in the surgical field. Any suitable agent such as those agents within the purview of those skilled in the art can be used in accordance with the present disclosure.

The filaments and sutures of the present disclosure may additionally include a needle at one end. In order to facilitate needle attachment to a suture of the present disclosure, conventional tipping agents can be applied to the braid. Two tipped ends of the suture may be desirable for attaching a needle to each end of the suture to provide a so-called double armed suture. The needle attachment can be made by any conventional method such as crimping, swaging, and the like.

In some cases, a tubular insertion device (not shown) may be utilized to introduce a barbed medical device in accordance with the present disclosure into tissue. Such a tubular insertion device may have a tubular body in which the barbed medical device of the present disclosure is disposed, as well as a distal end and a proximal end. In use, in some embodiments, the pointed end of a barbed suture of the present disclosure may be pushed with the distal end of the tubular insertion device through skin, tissue, and the like at an insertion point. The pointed end of the suture and the distal end of the tubular insertion device are pushed through the tissue until reaching an endpoint. The proximal end of the tubular insertion device is then gripped and pulled to remove the insertion device, leaving the barbed suture in place.

Barbed medical devices and placement methods suitable for use according to the present disclosure are well known in the art. For example, in embodiments, medical devices of the present disclosure may be utilized to provide lift to tissue, which may be desirable in certain cosmetic applications. In other embodiments, medical devices of the present disclosure may be utilized to close a tissue opening. In some embodiments, a procedure for closing tissue utilizing barbed staples include inserting a staple cartridge of barbed staples into a surgical stapler and firing the staple through the tissue to be joined. The surgical stapler may or may not include an anvil for deforming the staple. In some other embodiments, a procedure for closing tissue utilizing barbed sutures includes inserting a first end of a monofilament suture, optionally attached to a needle, at an insertion point through the body tissue. The first end of the suture may be pushed through body tissue until the first end extends out of the body tissue at an exit point. The first end of the monofilament suture may then be gripped and pulled to draw the first portion of the suture through the body tissue so that an outer surface of the elongated body (of the first portion) of the suture remains in direct contact with the body tissue between the point of insertion and exit point of the first end. As shown, for example in FIG. 10, the outer surface 630 of the elongated body 610 is in direct contact with tissue "t". The outer surface 630 may be in direct contact with tissue "t" for any length "L" of the elongated body and is not limited to the contact length "L" as shown in FIG. 10. The body tissue may then be manually grouped and advanced along at least one portion of the monofilament suture to provide the desired amount of lift.

The medical devices of the present disclosure may be utilized in any cosmetic, endoscopic or laparoscopic methods. In addition, sutures of the present disclosure may be utilized to attach one tissue to another including, but not limited to, attaching tissue to a ligament. Specific applications of cosmetic surgeries include, for example, facelifts, browlifts, thigh lifts, and breast lifts.

While the above description contains many specifics, these specifics should not be construed as limitations on the scope of the disclosure, but merely as exemplifications of embodiments thereof. Those skilled in the art will envision many other possibilities within the scope and spirit of the disclosure as defined by the claims appended hereto.

What is claimed is:

1. A compound barb staple comprising:
    a continuous body including a crown interconnecting a pair of legs, and having a substantially uniform diameter; and
    at least one barb extending from each of the legs, the at least one barb defining an inner surface having a complementary shape with an outer surface of the leg, the inner surface including a first portion disposed at a first orientation relative to a longitudinal axis of the leg and a second portion disposed at a second orientation relative to the longitudinal axis.

2. The compound barb staple according to claim 1, wherein the inner surface of the barb further comprises a third portion disposed at a third orientation relative to the longitudinal axis.

3. The compound barb staple according to claim 2, wherein at least one of the first, second, and third portions is substantially linear.

4. The compound barb staple according to claim 2, wherein at least one of the first, second, and third portions are at first, second, and third angles relative to respective longitudinal axes of each leg.

5. The compound barb staple according to claim 4, wherein the first angle is about 0 degrees to about 90 degrees.

6. The compound barb staple according to claim 5, wherein the first angle is about 30 degrees to about 40 degrees.

7. The compound barb staple according to claim 6, wherein the first angle is about 31 degrees to about 38 degrees.

8. The compound barb staple according to claim 4, wherein the second angle is about 0 degrees to about 90 degrees.

9. The compound barb staple according to claim 8, wherein the second angle is from about 1 degree to about 10 degrees.

10. The compound barb staple according to claim 9, wherein the second angle is from about 2 degrees to about 8 degrees.

11. The compound barb staple according to claim 4, wherein the third angle is about 0 degrees to about 90 degrees.

12. The compound barb staple according to claim 2, wherein at least one of the first, second, and third portions is substantially non-linear.

13. The compound barb staple according to claim 12, wherein the substantially non-linear portion is cut at a radius relative to the longitudinal axis of the leg.

14. The compound barb staple according to claim 1, wherein the crown and the pair of legs are formed from an absorbable or non-absorbable material.

15. The compound barb staple according to claim 14, wherein the-non-absorbable material is selected from the group consisting of titanium, stainless steel and alloys thereof.

16. The compound barb staple according to claim 14, wherein the non-absorbable material is selected from the group consisting of polyolefins, polyamides, polyamines, polyimines, polyesters, fluoropolymers, polyether-esters, polytetramethylene ether glycol, 1,4-butanediol, polyurethanes, copolymers, and combinations thereof.

17. The compound barb staple according to claim 14, wherein the absorbable material comprises a dissolvable metal.

18. The compound barb staple according to claim 14, wherein the absorbable material is selected from the group consisting of polyesters, polyorthoesters, polymer drugs, polyhydroxybutyrates, dioxanones, lactones, proteins, cat gut, collagens, carbonates, alkylene carbonates, caprolactone, glycolic acid, lactic acid, glycolide, lactide, homopolymers, copolymers, and combinations thereof.

19. The compound barb staple according to claim 1, further including a bioactive agent.

20. The compound barb staple according to claim 1, wherein the continuous body and the at least one barb are a monolithic structure.

21. The compound barb staple according to claim 1, wherein the at least one barb is made from a shape memory material which can be deformed into a temporary shape from a permanent shape, wherein the barb projects in a first position when in the temporary shape and in a second position, which is different from the first position, when in the permanent shape.

22. The compound barb staple according to claim 1, wherein each of the legs are deformable between an original configuration and a crimped configuration.

* * * * *